United States Patent
Luttrull et al.

(10) Patent No.: US 10,531,908 B2
(45) Date of Patent: Jan. 14, 2020

(54) METHOD FOR HEAT TREATING BIOLOGICAL TISSUES USING PULSED ENERGY SOURCES

(71) Applicant: Ojai Retinal Technology, LLC, Ojai, CA (US)

(72) Inventors: Jeffrey K. Luttrull, Ojai, CA (US); David B. Chang, Tustin, CA (US); Benjamin W. L. Margolis, Oakland, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 0 days.

(21) Appl. No.: 15/214,726

(22) Filed: Jul. 20, 2016

(65) Prior Publication Data

US 2016/0338757 A1 Nov. 24, 2016

Related U.S. Application Data

(63) Continuation-in-part of application No. 14/922,885, filed on Oct. 26, 2015, now Pat. No. 9,427,602, which
(Continued)

(51) Int. Cl.
*A61B 18/12* (2006.01)
*A61N 5/06* (2006.01)
(Continued)

(52) U.S. Cl.
CPC .......... *A61B 18/12* (2013.01); *A61F 9/00821* (2013.01); *A61N 5/025* (2013.01);
(Continued)

(58) Field of Classification Search
CPC ..... A61B 18/12; A61F 9/00821; A61N 5/025; A61N 5/045; A61N 5/0625; A61N 5/0603
(Continued)

(56) References Cited

U.S. PATENT DOCUMENTS

| 3,408,593 A | 10/1968 | Hurwitz, Jr. |
| 4,048,011 A | 9/1977 | Kovin et al. |

(Continued)

FOREIGN PATENT DOCUMENTS

| WO | 2006005038 A2 | 1/2006 |
| WO | 2007035855 A2 | 3/2007 |
| WO | 2007106521 A2 | 9/2007 |

OTHER PUBLICATIONS

Sramek et al, Non-damaging Retinal Phototherapy: Dynamic Range of Heat Shock Protein Expression. Investigative Ophthalmology & Visual Science, vol. 52, No. 3, Mar. 28, 2011, pp. 1780-1787 [online], [retrieved on Aug. 6, 2018]. Retrieved from the Internet <URL: https://iovs.arvojournals.org/article.aspx?articleid=2127223>.*

(Continued)

*Primary Examiner* — Gary Jackson
*Assistant Examiner* — Sebastian X Lukjan
(74) *Attorney, Agent, or Firm* — Kelly & Kelley, LLP

(57) ABSTRACT

A method for heat treating biological tissues includes providing a pulsed energy source having energy parameters selected so as to raise a target temperature to a level to achieve a therapeutic effect, while the average temperature rise of the tissue over a prolonged period of time is maintained at or below a predetermined level so as not to permanently damage the target tissue. Application of the pulsed energy source to the target tissue induces a heat shock response and stimulates heat shock protein activation in the target tissue so as to therapeutically treat the target tissue.

14 Claims, 25 Drawing Sheets

Related U.S. Application Data is a continuation-in-part of application No. 14/607,959, filed on Jan. 28, 2015, now Pat. No. 9,168,174, which is a continuation-in-part of application No. 13/798,523, filed on Mar. 13, 2013, now Pat. No. 10,219,947, which is a continuation-in-part of application No. 13/481,124, filed on May 25, 2012, now Pat. No. 9,381,115.

(60) Provisional application No. 62/153,616, filed on Apr. 28, 2015.

(51) Int. Cl.
| | | |
|---|---|---|
| *A61N 5/04* | (2006.01) | |
| *A61F 9/008* | (2006.01) | |
| *A61N 5/02* | (2006.01) | |
| *A61N 5/067* | (2006.01) | |
| *A61B 18/00* | (2006.01) | |
| *A61N 7/00* | (2006.01) | |

(52) U.S. Cl.
CPC ........... *A61N 5/045* (2013.01); *A61N 5/0603* (2013.01); *A61N 5/0625* (2013.01); *A61B 2018/00494* (2013.01); *A61F 9/00817* (2013.01); *A61F 2009/00863* (2013.01); *A61N 2005/063* (2013.01); *A61N 2005/0604* (2013.01); *A61N 2005/0667* (2013.01); *A61N 2005/0609* (2013.01); *A61N 2005/0659* (2013.01); *A61N 2005/0662* (2013.01); *A61N 2007/0004* (2013.01)

(58) Field of Classification Search
USPC .......................................................... 606/11
See application file for complete search history.

(56) References Cited

U.S. PATENT DOCUMENTS

| | | | |
|---|---|---|---|
| 4,176,325 A | 11/1979 | Kajimura et al. | |
| 4,194,114 A | 3/1980 | Pankratov et al. | |
| 4,410,365 A | 10/1983 | Glukhovsky et al. | |
| 4,695,733 A | 9/1987 | Pesavento | |
| 4,730,355 A | 3/1988 | Clark et al. | |
| 4,791,634 A | 12/1988 | Miyake | |
| 4,825,880 A | 5/1989 | Stauffer et al. | |
| 4,865,029 A | 9/1989 | Pankratov et al. | |
| 4,879,722 A | 11/1989 | Dixon et al. | |
| 4,930,504 A | 6/1990 | Diamantopoulos et al. | |
| 4,933,944 A | 6/1990 | McGraw | |
| 4,935,931 A | 6/1990 | McGraw | |
| 4,961,079 A | 10/1990 | Owens et al. | |
| 4,967,416 A | 10/1990 | Esterowitz et al. | |
| 5,037,421 A | 8/1991 | Boutacoff et al. | |
| 5,067,951 A | 11/1991 | Greve | |
| 5,085,492 A | 2/1992 | Kelsoe et al. | |
| 5,088,803 A | 2/1992 | Buzawa | |
| 5,147,354 A | 9/1992 | Boutacoff et al. | |
| 5,348,002 A | 9/1994 | Caro | |
| 5,372,595 A | 12/1994 | Gaasterland et al. | |
| 5,394,199 A | 2/1995 | Flower | |
| 5,430,756 A | 7/1995 | Hanihara | |
| 5,520,680 A | 5/1996 | Shapshay et al. | |
| 5,651,019 A | 7/1997 | Goldberg et al. | |
| 5,982,789 A | 11/1999 | Marshall et al. | |
| 6,050,990 A | 5/2000 | Thompson | |
| 6,066,128 A | 5/2000 | Bahmanyar et al. | |
| 6,156,028 A | 12/2000 | Prescott | |
| 6,208,769 B1 | 3/2001 | Pankratov | |
| 6,222,869 B1 | 4/2001 | Marshall et al. | |
| 6,259,952 B1 | 7/2001 | Sluijter et al. | |
| 6,327,291 B1 | 12/2001 | Marshall | |
| 6,377,599 B1 | 4/2002 | Marshall | |
| 6,514,278 B1* | 2/2003 | Hibst | A61B 18/203 606/11 |
| 6,540,391 B2 | 4/2003 | Lanzetta et al. | |
| 6,599,246 B1 | 7/2003 | Coffey et al. | |
| 6,681,185 B1 | 1/2004 | Young et al. | |
| 6,715,877 B2 | 4/2004 | Molebny | |
| 6,733,490 B1 | 5/2004 | Falsini et al. | |
| 6,813,942 B1 | 11/2004 | Vozhdaev et al. | |
| 6,889,695 B2 | 5/2005 | Pankratov et al. | |
| 7,227,196 B2 | 6/2007 | Burgener, II et al. | |
| 7,387,785 B1 | 6/2008 | Rudin et al. | |
| 7,452,081 B2 | 11/2008 | Wiltberger et al. | |
| 7,645,276 B2 | 1/2010 | Pankratov et al. | |
| 7,763,828 B2 | 7/2010 | Talwar et al. | |
| 7,766,903 B2 | 8/2010 | Blumenkranz et al. | |
| 7,766,904 B2 | 8/2010 | McGowan, Sr. et al. | |
| 7,771,417 B2 | 8/2010 | Telfair et al. | |
| 7,909,816 B2 | 3/2011 | Buzawa | |
| 2002/0120255 A1 | 8/2002 | Sotiropoulos et al. | |
| 2005/0049582 A1 | 3/2005 | DeBenedictis et al. | |
| 2006/0173512 A1 | 8/2006 | Barolet et al. | |
| 2007/0213792 A1* | 9/2007 | Yaroslavsky | A61N 5/0613 607/100 |
| 2007/0231255 A1* | 10/2007 | Barolet | A61K 31/375 424/1.11 |
| 2007/0233208 A1* | 10/2007 | Kurtz | A61N 5/0613 607/88 |
| 2008/0015553 A1 | 1/2008 | Zacharias | |
| 2008/0058783 A1* | 3/2008 | Altshuler | A61B 18/203 606/9 |
| 2008/0076958 A1 | 3/2008 | Britva et al. | |
| 2008/0077198 A1* | 3/2008 | Webb | A61N 5/0618 607/88 |
| 2009/0048586 A1 | 2/2009 | Krueger et al. | |
| 2009/0198309 A1* | 8/2009 | Gowda | A61B 18/1815 607/102 |
| 2010/0049180 A1* | 2/2010 | Wells | A61N 5/0616 606/12 |
| 2010/0082024 A1 | 4/2010 | Brannan et al. | |
| 2010/0092424 A1 | 4/2010 | Sanghvi et al. | |
| 2010/0100162 A1 | 4/2010 | Peyman | |
| 2010/0152716 A1 | 6/2010 | Previn et al. | |
| 2010/0168724 A1 | 7/2010 | Sramek et al. | |
| 2010/0249760 A1 | 9/2010 | Blumenkranz et al. | |
| 2010/0290007 A1 | 11/2010 | Van de Velde | |
| 2011/0196350 A1 | 8/2011 | Friedman et al. | |
| 2011/0306956 A1* | 12/2011 | Islam | A61B 18/20 606/15 |
| 2014/0121631 A1* | 5/2014 | Bean | A61N 5/0616 604/500 |
| 2014/0148735 A1 | 5/2014 | Nau, Jr. | |
| 2014/0194958 A1 | 7/2014 | Chabal et al. | |
| 2015/0157498 A1 | 6/2015 | Luttrull et al. | |
| 2016/0082294 A1 | 3/2016 | Luttrull et al. | |

OTHER PUBLICATIONS

International Search Report for the International application No. PCT/US2016/46043 dated Dec. 27, 2016.

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

Small Beam Diameter Scanning Galvo Mirror Systems; Thorlabs; 1999-2013, 4 pgs.

(56) References Cited

OTHER PUBLICATIONS

International Search Report for the International application No. PCT/US2015/60893, dated Mar. 18, 2016.
International Search Report for the International Application No. PCT/US2017/44337 dated Jan. 9, 2018.

* cited by examiner

METHOD FOR HEAT TREATING BIOLOGICAL TISSUES USING PULSED ENERGY SOURCES

RELATED APPLICATIONS

This application is a continuation-in-part of U.S. application Ser. No. 14/922,885, filed on Oct. 26, 2015 (which claims the benefit of U.S. Application No. 62/153,616, filed on Apr. 28, 2015), which is a continuation-in-part of U.S. application Ser. No. 14/607,959 filed on Jan. 28, 2015, now U.S. Pat. No. 9,168,174, which is a continuation-in-part of U.S. application Ser. No. 13/798,523, filed on Mar. 13, 2013, which is a continuation-in-part of U.S. application Ser. No. 13/481,124, filed on May 25, 2012, now U.S. Pat. No. 9,381,115.

BACKGROUND OF THE INVENTION

The present invention is generally directed to a method for heat treating biological tissues. More particularly, the present invention is directed to a method for applying a pulsed energy source to biological tissue to stimulate activation of heat shock proteins and facilitate protein repair without damaging the tissue.

The inventors have discovered that there is a therapeutic effect to biological tissue, and particularly damaged or diseased biological tissue, by controllably elevating the tissue temperature up to a predetermined temperature range while maintaining the average temperature rise of the tissue over several minutes at or below a predetermined level so as not to permanently damage the target tissue. It is believed that raising the tissue temperature in such a controlled manner selectively stimulates heat shock protein activation and/or production and facilitation of protein repair, which serves as a mechanism for therapeutically treating the tissue.

Heat shock proteins (HSPs) are a family of proteins that are produced by cells in response to exposure to stressful conditions. Production of high levels of heat shock proteins can be triggered by exposure to different kinds of environmental stress conditions, such as infection, inflammation, exercise, exposure of the cell to toxins, starvation, hypoxia, or water deprivation.

It is known that heat shock proteins play a role in responding to a large number of abnormal conditions in body tissues, including viral infection, inflammation, malignant transformations, exposure to oxidizing agents, cytotoxins, and anoxia. Several heat shock proteins function as intra-cellular chaperones for other proteins and members of the HSP family are expressed or activated at low to moderate levels because of their essential role in protein maintenance and simply monitoring the cell's proteins even under non-stressful conditions. These activities are part of a cell's own repair system, called the cellular stress response or the heat-shock response.

Heat shock proteins are typically named according to their molecular weight. For example, Hsp60, Hsp70 and Hsp80 refer to the families of heat shock proteins on the order of 60, 70 and 80 kilodaltons in size, respectively. They act in a number of different ways. For example, Hsp70 has peptide-binding and ATPase domains that stabilize protein structures in unfolded and assembly-competent states. Mitochondrial Hsp60s form ring-shaped structures facilitating the assembly of proteins into native states. Hsp90 plays a suppressor regulatory role by associating with cellular tyrosine kinases, transcription factors, and glucocorticoid receptors. Hsp27 suppresses protein aggregation.

Hsp70 heat shock proteins are a member of extracellular and membrane bound heat-shock proteins which are involved in binding antigens and presenting them to the immune system. Hsp70 has been found to inhibit the activity of influenza A virus ribonucleoprotein and to block the replication of the virus. Heat shock proteins derived from tumors elicit specific protective immunity. Experimental and clinical observations have shown that heat shock proteins are involved in the regulation of autoimmune arthritis, type 1 diabetes, mellitus, arterial sclerosis, multiple sclerosis, and other autoimmune reactions.

Accordingly, it is believed that it is advantageous to be able to selectively and controllably raise a target tissue temperature up to a predetermined temperature range over a short period of time, while maintaining the average temperature rise of the tissue at a predetermined temperature over a longer period of time. It is believed that this induces the heat shock response in order to increase the number or activity of heat shock proteins in body tissue in response to infection or other abnormalities. However, this must be done in a controlled manner in order not to damage or destroy the tissue or the area of the body being treated. The present invention fulfills these needs, and provides other related advantages.

SUMMARY OF THE INVENTION

The present invention is directed to a method for heat treating biological tissues by applying a pulsed energy source to the target tissue to therapeutically treat the target tissue. The pulsed energy source has energy parameters including wavelength or frequency, duty cycle and pulse train duration. The energy parameters are selected so as to raise a target tissue temperature up to 11° C. to achieve a therapeutic effect, wherein the average temperature rise of the tissue over several minutes is maintained at or below a predetermined level so as not to permanently damage the target tissue.

The energy source parameters may be selected so that the target tissue temperature is raised between approximately 6° C. to 11° C. at least during application of the pulsed energy source to the target tissue. The average temperature rise of the target tissue over several minutes is maintained at 6° C. or less, such as at approximately 1° C. or less over several minutes.

The pulsed energy source energy parameters are selected so that approximately 20 to 40 joules of energy is absorbed by each cubic centimeter of the target tissue. Applying the pulsed energy source to the target tissue induces a heat shock response and stimulates heat shock protein activation in the target tissue without damaging the target tissue.

A device may be inserted into a cavity of the body in order to apply the pulsed energy to the tissue. The pulsed energy may be applied to an exterior area of a body which is adjacent to the target tissue, or has a blood supply close to a surface of the exterior area of the body.

The pulsed energy source may comprise a radiofrequency. The radiofrequency may be between approximately 3 to 6 megahertz (MHz). It may have a duty cycle of between approximately 2.5% to 5%. It may have a pulsed train duration of between approximately 0.2 to 0.4 seconds. The radiofrequency may be generated with a device having a coil radii of between approximately 2 and 6 mm and approximately 13 and 57 amp turns.

The pulsed energy source may comprise a microwave frequency of between 10 to 20 gigahertz (GHz). The microwave may have a pulse train duration of approximately between 0.2 and 0.6 seconds. The microwave may have a duty cycle of between approximately 2% and 5%. The microwave may have an average power of between approximately 8 and 52 watts.

The pulsed energy source may comprise a pulsed light beam, such as a laser light. The light beam may have a wavelength of between approximately 530 nm to 1300 nm, and more preferably between 800 nm and 1000 nm. The pulsed light beam may have a power of between approximately 0.5 and 74 watts. The pulsed light beam has a duty cycle of less than 10%, and preferably between 2.5% and 5%. The pulsed light beam may have a pulse train duration of approximately 0.1 and 0.6 seconds.

The pulsed energy source may comprise a pulsed ultrasound. The ultrasound has a frequency of between approximately 1 and 5 MHz. The ultrasound has a train duration of approximately 0.1 and 05 seconds. The ultrasound may have a duty cycle of between approximately 2% and 10%. The ultrasound has a power of between approximately 0.46 and 28.6 watts.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1A:
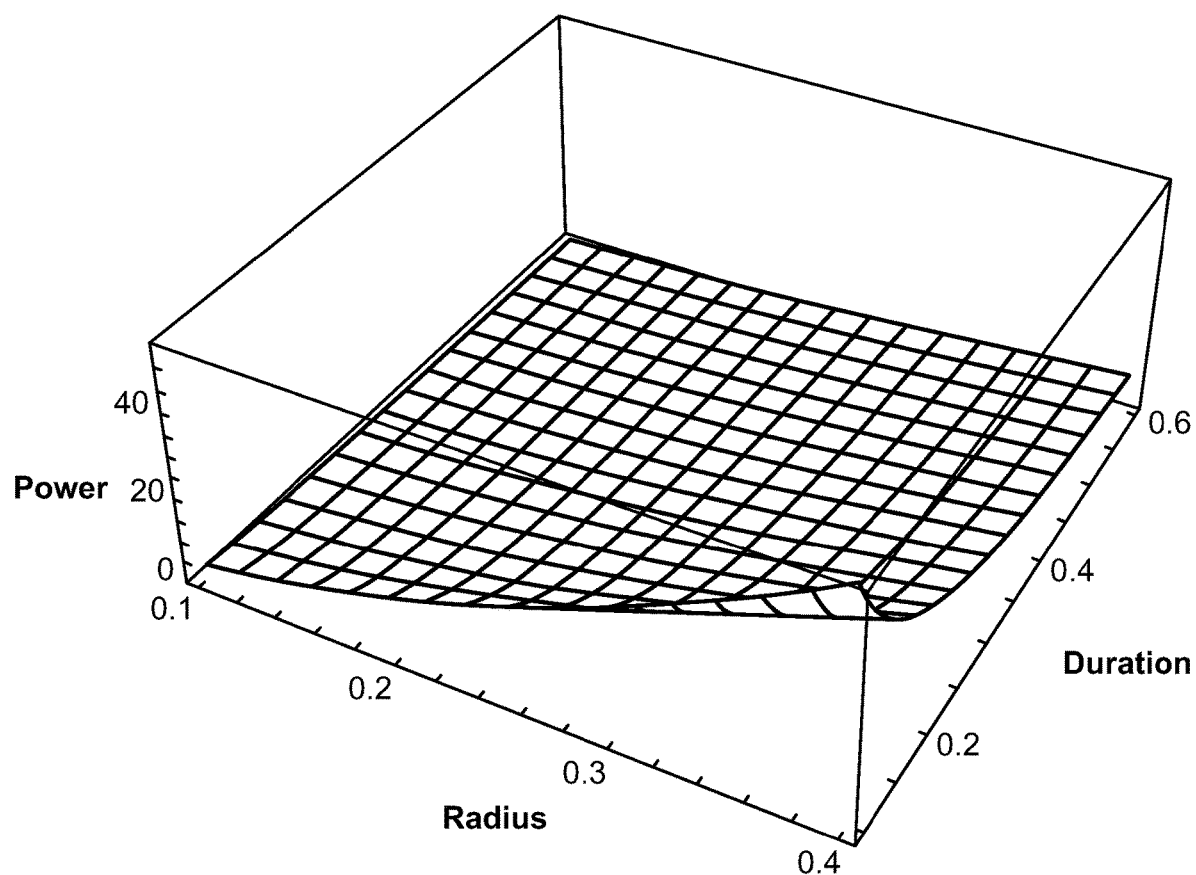
FIGS. 1A and 1B are graphs illustrating the average power of a laser source compared to a source radius and pulse train duration of the laser.

As shown in the accompanying drawings, and as more fully described herein, the present invention is directed to a system and method for delivering a pulsed energy source, such as laser, ultrasound, ultraviolet radiofrequency, microwave radiofrequency and the like, having energy parameters selected to cause a thermal time-course in tissue to raise the tissue temperature over a short period of time to a sufficient level to achieve a therapeutic effect while maintaining an average tissue temperature over a prolonged period of time below a predetermined level so as to avoid permanent tissue damage. It is believed that the creation of the thermal time-course stimulates heat shock protein activation or production and facilitates protein repair without causing any damage.

The inventors of the present invention have discovered that electromagnetic radiation, in the form of various wavelengths of laser light, can be applied to retinal tissue in a manner that does not destroy or damage the retinal tissue while achieving beneficial effects on eye diseases. It is believed that this may be due, at least in part, to the stimulation and activation of heat shock proteins and the facilitation of protein repair in the retinal tissue. This is disclosed in U.S. patent application Ser. No. 14/607,959 filed Jan. 28, 2015, Ser. No. 13/798,523 filed Mar. 13, 2013, and Ser. No. 13/481,124 filed May 25, 2012, the contents of which are hereby incorporated by reference as if made in full.

The inventors have found that a laser light beam can be generated that is therapeutic, yet sublethal to retinal tissue cells and thus avoids damaging photocoagulation in the retinal tissue which provides preventative and protective treatment of the retinal tissue of the eye. Various parameters of the light beam must be taken into account and selected so that the combination of the selected parameters achieve the therapeutic effect while not permanently damaging the tissue. These parameters include laser wavelength, radius of the laser source, average laser power, total pulse duration, and duty cycle of the pulse train.

The selection of these parameters may be determined by requiring that the Arrhenius integral for HSP activation be greater than 1 or unity. Arrhenius integrals are used for analyzing the impacts of actions on biological tissue. See, for instance, The CRC Handbook of Thermal Engineering, ed. Frank Kreith, Springer Science and Business Media (2000). At the same time, the selected parameters must not permanently damage the tissue. Thus, the Arrhenius integral for damage may also be used, wherein the solved Arrhenius integral is less than 1 or unity. Alternatively, the FDA/FCC constraints on energy deposition per unit gram of tissue and temperature rise as measured over periods of minutes be satisfied so as to avoid permanent tissue damage. The FDA/FCC requirements on energy deposition and temperature rise are widely used and can be referenced, for example, at www.fda.gov/medicaldevices/deviceregulationandguidance/guidancedocuments/ucm073817.htm#attacha for electromagnetic sources, and Anastosio and P. LaRivero, ed., Emerging Imaging Technologies. CRC Press (2012), for ultrasound sources. Generally speaking, tissue temperature rises of between 6° C. and 11° C. can create therapeutic effect, such as by activating heat shock proteins, whereas maintaining the average tissue temperature over a prolonged period of time, such as over several minutes, such as six minutes, below a predetermined temperature, such as 6° C. and even 1° C. or less in certain circumstances, will not permanently damage the tissue.

The inventors have discovered that generating a subthreshold, sublethal micropulse laser light beam which has a wavelength greater than 532 nm and a duty cycle of less than 10% at a predetermined intensity or power and a predetermined pulse length or exposure time creates desirable retinal photostimulation without any visible burn areas or tissue destruction. More particularly, a laser light beam having a wavelength of between 550 nm-1300 nm, and in a particularly preferred embodiment between 810 nm and 1000 nm, having a duty cycle of approximately 2.5%-5% and a predetermined intensity or power (such as between 100-590 watts per square centimeter at the retina or approximately 1 watt per laser spot for each treatment spot at the retina) and a predetermined pulse length or exposure time (such as between 100 and 600 milliseconds or less) creates a sublethal, "true subthreshold" retinal photostimulation in which all areas of the retinal pigment epithelium exposed to the laser irradiation are preserved and available to contribute therapeutically. In other words, the inventors have found that raising the retinal tissue at least up to a therapeutic level but below a cellular or tissue lethal level recreates the benefit of the halo effect of the prior art methods without destroying, burning or otherwise damaging the retinal tissue. This is referred to herein as subthreshold diode micropulse laser treatment (SDM).

As SDM does not produce laser-induced retinal damage (photocoagulation), and has no known adverse treatment effect, and has been reported to be an effective treatment in a number of retinal disorders (including diabetic macular edema (DME) proliferative diabetic retinopathy (PDR), macular edema due to branch retinal vein occlusion (BRVO), central serous chorioretinopathy (CSR), reversal of drug tolerance, and prophylactic treatment of progressive degenerative retinopathies such as dry age-related macular degeneration, Stargardts' disease, cone dystrophies, and retinitis pigmentosa. The safety of SDM is such that it may be used transfoveally in eyes with 20/20 visual acuity to reduce the risk of visual loss due to early fovea-involving DME.

A mechanism through which SDM might work is the generation or activation of heat shock proteins (HSPs). Despite a near infinite variety of possible cellular abnormalities, cells of all types share a common and highly conserved mechanism of repair: heat shock proteins (HSPs). HSPs are elicited almost immediately, in seconds to minutes, by almost any type of cell stress or injury. In the absence of lethal cell injury, HSPs are extremely effective at repairing and returning the viable cell toward a more normal functional state. Although HSPs are transient, generally peaking in hours and persisting for a few days, their effects may be long lasting. HSPs reduce inflammation, a common factor in many disorders.

Laser treatment can induce HSP production or activation and alter cytokine expression. The more sudden and severe the non-lethal cellular stress (such as laser irradiation), the more rapid and robust HSP activation. Thus, a burst of repetitive low temperature thermal spikes at a very steep rate of change (~7° C. elevation with each 100 μs micropulse, or 70,000° C./sec) produced by each SDM exposure is especially effective in stimulating activation of HSPs, particularly compared to non-lethal exposure to subthreshold treatment with continuous wave lasers, which can duplicate only the low average tissue temperature rise.

Laser wavelengths below 550 nm produce increasingly cytotoxic photochemical effects. At 810 nm, SDM produces photothermal, rather than photochemical, cellular stress. Thus, SDM is able to affect the tissue without damaging it. The clinical benefits of SDM are thus primarily produced by sub-morbid photothermal cellular HSP activation. In dysfunctional cells, HSP stimulation by SDM results in normalized cytokine expression, and consequently improved structure and function. The therapeutic effects of this "low-intensity" laser/tissue interaction are then amplified by "high-density" laser application, recruiting all the dysfunctional cells in the targeted tissue area by densely/confluently treating a large tissue area, including all areas of pathology, thereby maximizing the treatment effect. These principles define the treatment strategy of SDM described herein.

Because normally functioning cells are not in need of repair, HSP stimulation in normal cells would tend to have no notable clinical effect. The "patho-selectivity" of near infrared laser effects, such as SDM, affecting sick cells but not affecting normal ones, on various cell types is consistent with clinical observations of SDM. SDM has been reported to have a clinically broad therapeutic range, unique among retinal laser modalities, consistent with American National Standards Institute "Maximum Permissible Exposure" predictions. While SDM may cause direct photothermal effects such as entropic protein unfolding and disaggregation, SDM appears optimized for clinically safe and effective stimulation of HSP-mediated repair.

As noted above, while SDM stimulation of HSPs is non-specific with regard to the disease process, the result of HSP mediated repair is by its nature specific to the state of the dysfunction. HSPs tend to fix what is wrong, whatever that might be. Thus, the observed effectiveness of SDM in retinal conditions as widely disparate as BRVO, DME, PDR, CSR, age-related and genetic retinopathies, and drug-tolerant NAMD. Conceptually, this facility can be considered a sort of "Reset to Default" mode of SDM action. For the wide range of disorders in which cellular function is critical, SDM normalizes cellular function by triggering a "reset" (to the "factory default settings") via HSP-mediated cellular repair.

The inventors have found that SDM treatment of patients suffering from age-related macular degeneration (AMD) can slow the progress or even stop the progression of AMD. Most of the patients have seen significant improvement in dynamic functional log MAR mesoptic visual acuity and mesoptic contrast visual acuity after the SDM treatment. It is believed that SDM works by targeting, preserving, and "normalizing" (moving toward normal) function of the retinal pigment epithelium (RPE).

SDM has also been shown to stop or reverse the manifestations of the diabetic retinopathy disease state without treatment-associated damage or adverse effects, despite the persistence of systemic diabetes mellitus. On this basis it is hypothesized that SDM might work by inducing a return to more normal cell function and cytokine expression in diabetes-affected RPE cells, analogous to hitting the "reset" button of an electronic device to restore the factory default settings. Based on the above information and studies, SDM treatment may directly affect cytokine expression via heat shock protein (HSP) activation in the targeted tissue.

As heat shock proteins play a role in responding to a large number of abnormal conditions in body tissue other than eye tissue, it is believed that similar systems and methodologies can be advantageously used in treating such abnormal conditions, infections, etc. As such, the present invention is directed to the controlled application of ultrasound or electromagnetic radiation to treat abnormal conditions including inflammations, autoimmune conditions, and cancers that are accessible by means of fiber optics of endoscopes or surface probes as well as focused electromagnetic/sound waves. For example, cancers on the surface of the prostate that have the largest threat of metastasizing can be accessed by means of fiber optics in a proctoscope. Colon tumors can be accessed by an optical fiber system, like those used in colonoscopy.

As indicated above, subthreshold diode micropulse laser (SDM) photostimulation has been effective in stimulating direct repair of slightly misfolded proteins in eye tissue. Besides HSP activation, another way this may occur is because the spikes in temperature caused by the micropulses in the form of a thermal time-course allows diffusion of water inside proteins, and this allows breakage of the peptide-peptide hydrogen bonds that prevent the protein from returning to its native state. The diffusion of water into proteins results in an increase in the number of restraining hydrogen bonds by a factor on the order of a thousand. Thus, it is believed that this process could be applied to other diseases advantageously as well.

As explained above, the energy source to be applied to the target tissue will have energy and operating parameters which must be determined and selected so as to achieve the therapeutic effect while not permanently damaging the tissue. Using a light beam energy source, such as a laser light beam, as an example, the laser wavelength, duty cycle and total pulse train duration parameters must be taken into account. Other parameters which can be considered include the radius of the laser source as well as the average laser power. Adjusting or selecting one of these parameters can have an effect on at least one other parameter.

Figure 1B:
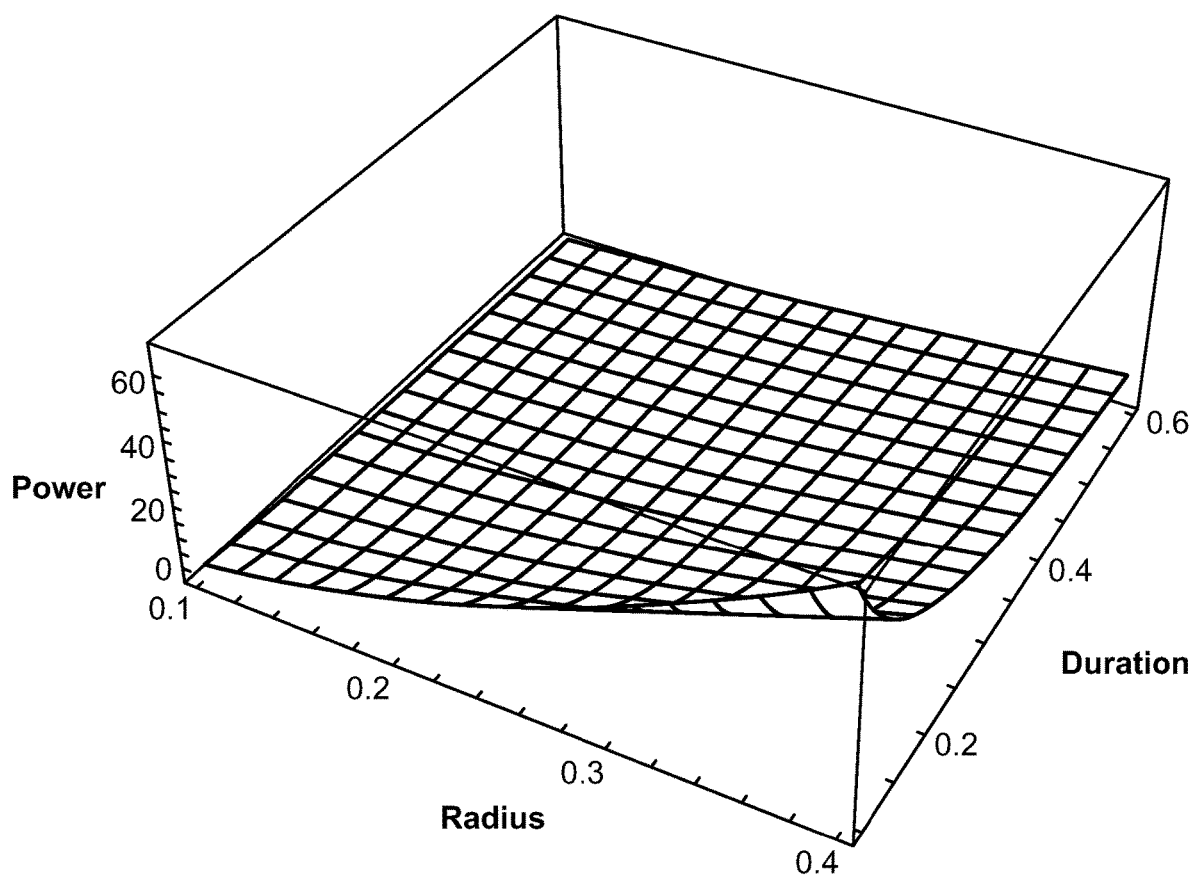

FIGS. 1A and 1B illustrate graphs showing the average power in watts as compared to the laser source radius (between 0.1 cm and 0.4 cm) and pulse train duration (between 0.1 and 0.6 seconds). FIG. 1A shows a wavelength of 880 nm, whereas FIG. 1B has a wavelength of 1000 nm. It can be seen in these figures that the required power decreases monotonically as the radius of the source decreases, as the total train duration increases, and as the wavelength decreases. The preferred parameters for the radius of the laser source is 1 mm-4 mm. For a wavelength of 880 nm, the minimum value of power is 0.55 watts, with a radius of the laser source being 1 mm, and the total pulse train duration being 600 milliseconds. The maximum value of power for the 880 nm wavelength is 52.6 watts when the laser source radius is 4 mm and the total pulse drain duration is 100 milliseconds. However, when selecting a laser having a wavelength of 1000 nm, the minimum power value is 0.77 watts with a laser source radius of 1 mm and a total pulse train duration of 600 milliseconds, and a maximum power value of 73.6 watts when the laser source radius is 4 mm and the total pulse duration is 100 milliseconds. The corresponding peak powers, during an individual pulse, are obtained from the average powers by dividing by the duty cycle.

The volume of the tissue region to be heated is determined by the wavelength, the absorption length in the relevant tissue, and by the beam width. The total pulse duration and the average laser power determine the total energy delivered to heat up the tissue, and the duty cycle of the pulse train gives the associated spike, or peak, power associated with the average laser power. Preferably, the pulsed energy source energy parameters are selected so that approximately 20 to 40 joules of energy is absorbed by each cubic centimeter of the target tissue.

The absorption length is very small in the thin melanin layer in the retinal pigmented epithelium. In other parts of the body, the absorption length is not generally that small. In wavelengths ranging from 400 nm to 2000 nm, the penetration depth and skin is in the range of 0.5 mm to 3.5 mm. The penetration depth into human mucous tissues in the range of 0.5 mm to 6.8 mm. Accordingly, the heated volume will be limited to the exterior or interior surface where the radiation source is placed, with a depth equal to the penetration depth, and a transverse dimension equal to the transverse dimension of the radiation source. Since the light beam energy source is used to treat diseased tissues near external surfaces or near internal accessible surfaces, a source radii of between 1 mm to 4 mm and operating a wavelength of 880 nm yields a penetration depth of approximately 2.5 mm and a wavelength of 1000 nm yields a penetration depth of approximately 3.5 mm.

Figure 2A:
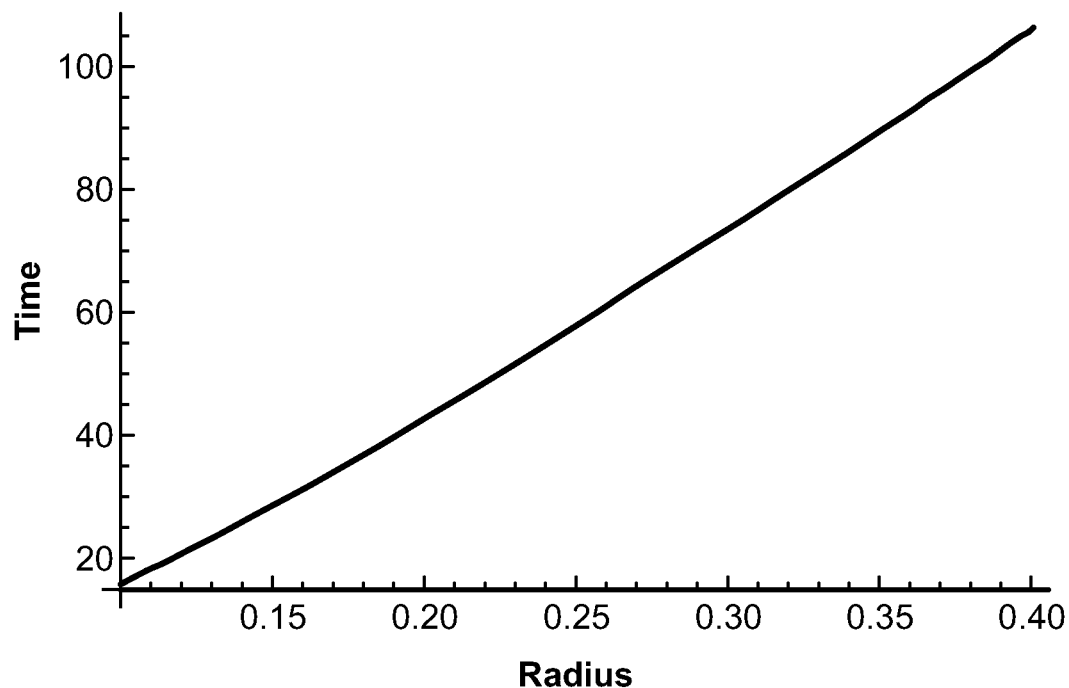
FIGS. 2A and 2B are graphs illustrating the time for the temperature to decay depending upon the laser source radius and wavelength.
Figure 2B:
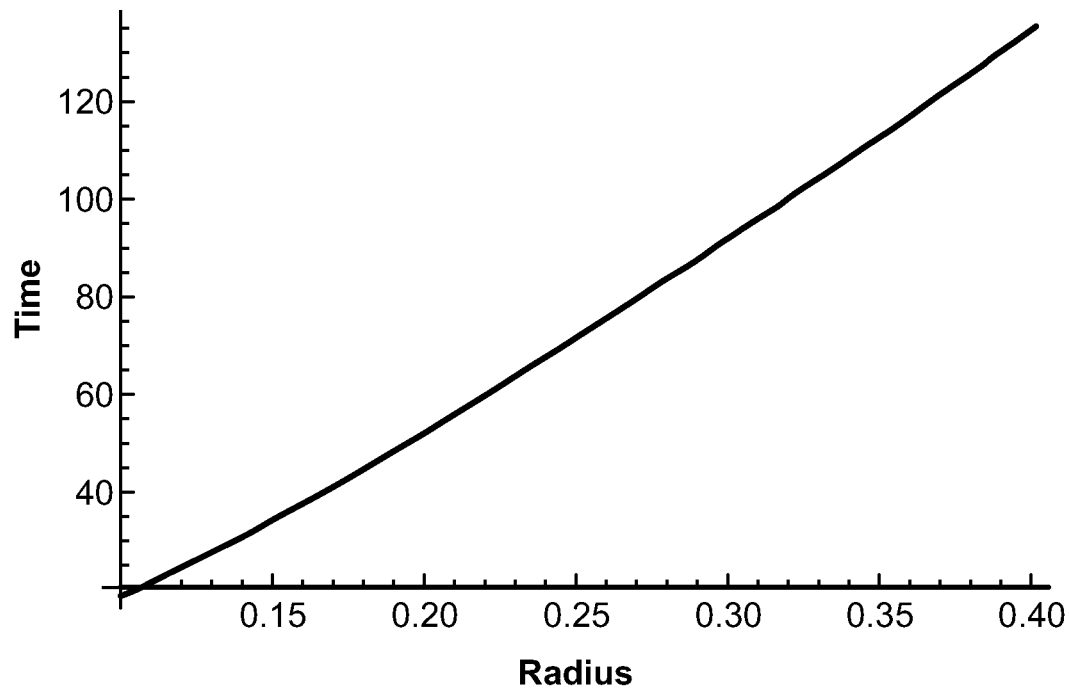

It has been determined that the target tissue can be heated to up to approximately 11° C. for a short period of time, such as less than one second, to create the therapeutic effect of the invention while maintaining the target tissue average temperature to a lower temperature range, such as less than 6° C. or even 1° C. or less over a prolonged period of time, such as several minutes. The selection of the duty cycle and the total pulse train duration provide time intervals in which the heat can dissipate. A duty cycle of less than 10%, and preferably between 2.5% and 5%, with a total pulse duration of between 100 milliseconds and 600 milliseconds has been found to be effective. FIGS. 2A and 2B illustrate the time to decay from 10° C. to 1° C. for a laser source having a radius of between 0.1 cm and 0.4 cm with the wavelength being 880 nm in FIG. 2A and 1000 nm in FIG. 2B. It can be seen that the time to decay is less when using a wavelength of 880 nm, but either wavelength falls within the acceptable requirements and operating parameters to achieve the benefits of the present invention while not causing permanent tissue damage.

It has been found that the average temperature rise of the desired target region increasing at least 6° C. and up to 11° C., and preferably approximately 10° C., during the total irradiation period results in HSP activation. The control of the target tissue temperature is determined by choosing source and target parameters such that the Arrhenius integral for HSP activation is larger than 1, while at the same time assuring compliance with the conservative FDA/FCC requirements for avoiding damage or a damage Arrhenius integral being less than 1.

In order to meet the conservative FDA/FCC constraints to avoid permanent tissue damage, for light beams, and other electromagnetic radiation sources, the average temperature rise of the target tissue over any six-minute period is 1° C. or less. The phrase "average temperature rise" as used herein is the target tissue total temperature increase over several minutes, such as up to six minutes, comparing the initial target tissue temperature before application of the pulsed energy source and the target tissue temperature several minutes, such as six minutes, after the application of the pulsed energy source to the target tissue. FIGS. 2A and 2B above illustrate the typical decay times required for the temperature in the heated target region to decrease by thermal diffusion from a temperature rise of approximately 10° C. to 1° C. as can be seen in FIG. 2A when the wavelength is 880 nm and the source diameter is 1 millimeter, the temperature decay time is 16 seconds. The temperature decay time is 107 seconds when the source diameter is 4 mm. As shown in FIG. 2B, when the wavelength is 1000 nm, the temperature decay time is 18 seconds when the source diameter is 1 mm and 136 seconds when the source diameter is 4 mm. This is well within the time of the average temperature rise being maintained over the course of several minutes, such as 6 minutes or less. While the target tissue's temperature is raised, such as to approximately 10° C., very quickly, such as in a fraction of a second during the application of the energy source to the tissue, the relatively low duty cycle provides relatively long periods of time between the pulses of energy applied to the tissue and the relatively short pulse train duration ensure sufficient temperature diffusion and decay within a relatively short period of time comprising several minutes, such as 6 minutes or less, that there is no permanent tissue damage.

The parameters differ for the individual energy sources, including microwave, infrared lasers, radiofrequency and ultrasound, because the absorption properties of tissues differ for these different types of energy sources. The tissue water content can vary from one tissue type to another, however, there is an observed uniformity of the properties of tissues at normal or near normal conditions which has allowed publication of tissue parameters that are widely used by clinicians in designing treatments. Below are tables illustrating the properties of electromagnetic waves in biological media, with Table 1 relating to muscle, skin and tissues with high water content, and Table 2 relating to fat, bone and tissues with low water content.

TABLE 1

Properties of Electromagnetic Waves in Biological Media: Muscle, Skin, and Tissues with High Water Content

| Frequency (MHz) | Wavelength in Air (cm) | Dielectric Constant $\in_H$ | Conductivity $\sigma_H$ (mho/m) | Wavelength $\lambda_H$ (cm) | Depth of Penetration (cm) | Reflection Coefficient Air-Muscle Interface r | Reflection Coefficient Air-Muscle Interface ø | Reflection Coefficient Muscle-Fat Interface r | Reflection Coefficient Muscle-Fat Interface ø |
|---|---|---|---|---|---|---|---|---|---|
| 1 | 30000 | 2000 | 0.400 | 436 | 91.3 | 0.982 | +179 | | |
| 10 | 3000 | 160 | 0.625 | 118 | 21.6 | 0.956 | +178 | | |
| 27.12 | 1106 | 113 | 0.612 | 68.1 | 14.3 | 0.925 | +177 | 0.651 | −11.13 |
| 40.68 | 738 | 97.3 | 0.693 | 51.3 | 11.2 | 0.913 | +176 | 0.652 | −10.21 |
| 100 | 300 | 71.7 | 0.889 | 27 | 6.66 | 0.881 | +175 | 0.650 | −7.96 |
| 200 | 150 | 56.5 | 1.28 | 16.6 | 4.79 | 0.844 | +175 | 0.612 | −8.06 |
| 300 | 100 | 54 | 1.37 | 11.9 | 3.89 | 0.825 | +175 | 0.592 | −8.14 |
| 433 | 69.3 | 53 | 1.43 | 8.76 | 3.57 | 0.803 | +175 | 0.562 | −7.06 |
| 750 | 40 | 52 | 1.54 | 5.34 | 3.18 | 0.779 | +176 | 0.532 | −5.69 |
| 915 | 32.8 | 51 | 1.60 | 4.46 | 3.04 | 0.772 | +177 | 0.519 | −4.32 |
| 1500 | 20 | 49 | 1.77 | 2.81 | 2.42 | 0.761 | +177 | 0.506 | −3.66 |
| 2450 | 12.2 | 47 | 2.21 | 1.76 | 1.70 | 0.754 | +177 | 0.500 | −3.88 |
| 3000 | 10 | 46 | 2.26 | 1.45 | 1.61 | 0.751 | +178 | 0.495 | −3.20 |
| 5000 | 6 | 44 | 3.92 | 0.89 | 0.788 | 0.749 | +177 | 0.502 | −4.95 |
| 5800 | 5.17 | 43.3 | 4.73 | 0.775 | 0.720 | 0.746 | +177 | 0.502 | −4.29 |
| 8000 | 3.75 | 40 | 7.65 | 0.578 | 0.413 | 0.744 | +176 | 0.513 | −6.65 |
| 10000 | 3 | 39.9 | 10.3 | 0.464 | 0.343 | 0.743 | +176 | 0.518 | −5.95 |

TABLE 2

Properties of Electromagnetic Waves in Biological Media: Fat, Bone, and Tissues with Low Water Content

| Frequency (MHz) | Wavelength in Air (cm) | Dielectric Constant $\in_L$ | Conductivity $\sigma_L$ (mmho/m) | Wavelength $\lambda_L$ (cm) | Depth of Penetration (cm) | Reflection Coefficient Air-Fat Interface r | Reflection Coefficient Air-Fat Interface ø | Reflection Coefficient Fat-Muscle Interface r | Reflection Coefficient Fat-Muscle Interface ø |
|---|---|---|---|---|---|---|---|---|---|
| 1 | 30000 | | | | | | | | |
| 10 | 3000 | | | | | | | | |
| 27.12 | 1106 | 20 | 10.9-43.2 | 241 | 159 | 0.660 | +174 | 0.651 | +169 |
| 40.68 | 738 | 14.6 | 12.6-52.8 | 187 | 118 | 0.617 | +173 | 0.652 | +170 |

TABLE 2-continued

Properties of Electromagnetic Waves in Biological Media: Fat, Bone, and Tissues with Low Water Content

| Frequency (MHz) | Wavelength in Air (cm) | Dielectric Constant $\varepsilon_L$ | Conductivity $\sigma_L$, (mmho/m) | Wavelength $\lambda_L$ (cm) | Depth of Penetration (cm) | Reflection Coefficient Air-Fat Interface r | ø | Fat-Muscle Interface r | ø |
|---|---|---|---|---|---|---|---|---|---|
| 100 | 300 | 7.45 | 19.1-75.9 | 106 | 60.4 | 0.511 | +168 | 0.650 | +172 |
| 200 | 150 | 5.95 | 25.8-94.2 | 59.7 | 39.2 | 0.458 | +168 | 0.612 | +172 |
| 300 | 100 | 5.7 | 31.6-107 | 41 | 32.1 | 0.438 | +169 | 0.592 | +172 |
| 433 | 69.3 | 5.6 | 37.9-118 | 28.8 | 26.2 | 0.427 | +170 | 0.562 | +173 |
| 750 | 40 | 5.6 | 49.8-138 | 16.8 | 23 | 0.415 | +173 | 0.532 | +174 |
| 915 | 32.8 | 5.6 | 55.6-147 | 13.7 | 17.7 | 0.417 | +173 | 0.519 | +176 |
| 1500 | 20 | 5.6 | 70.8-171 | 8.41 | 13.9 | 0.412 | +174 | 0.506 | +176 |
| 2450 | 12.2 | 5.5 | 96.4-213 | 5.21 | 11.2 | 0.406 | +176 | 0.500 | +176 |
| 3000 | 10 | 5.5 | 110-234 | 4.25 | 9.74 | 0.406 | +176 | 0.495 | +177 |
| 5000 | 6 | 5.5 | 162-309 | 2.63 | 6.67 | 0.393 | +176 | 0.502 | +175 |
| 5900 | 5.17 | 5.05 | 186-338 | 2.29 | 5.24 | 0.388 | +176 | 0.502 | +176 |
| 8000 | 3.75 | 4.7 | 255-431 | 1.73 | 4.61 | 0.371 | +176 | 0.513 | +173 — |
| 10000 | 3 | 4.5 | 324-549 | 1.41 | 3.39 | 0.363 | +175 | 0.518 | +174, — |

The absorption lengths of radiofrequency in body tissue are long compared to body dimensions. Consequently, the heated region is determined by the dimensions of the coil that is the source of the radiofrequency energy rather than by absorption lengths. Long distances r from a coil the magnetic (near) field from a coil drops off as $1/r^3$. At smaller distances, the electric and magnetic fields can be expressed in terms of the vector magnetic potential, which in turn can be expressed in closed form in terms of elliptic integrals of the first and second kind. The heating occurs only in a region that is comparable in size to the dimensions of the coil source itself. Accordingly, if it is desired to preferentially heat a region characterized by a radius, the source coil will be chosen to have a similar radius. The heating drops off very rapidly outside of a hemispherical region of radius because of the $1/r^3$ drop off of the magnetic field. Since it is proposed to use the radiofrequency the diseased tissue accessible only externally or from inner cavities, it is reasonable to consider a coil radii of between approximately 2 to 6 mm.

The radius of the source coil(s) as well as the number of ampere turns (NI) in the source coils give the magnitude and spatial extent of the magnetic field, and the radiofrequency is a factor that relates the magnitude of the electric field to the magnitude of the magnetic field. The heating is proportional to the product of the conductivity and the square of the electric field. For target tissues of interest that are near external or internal surfaces, the conductivity is that of skin and mucous tissue. The duty cycle of the pulse train as well as the total train duration of a pulse train are factors which affect how much total energy is delivered to the tissue.

Figure 3:
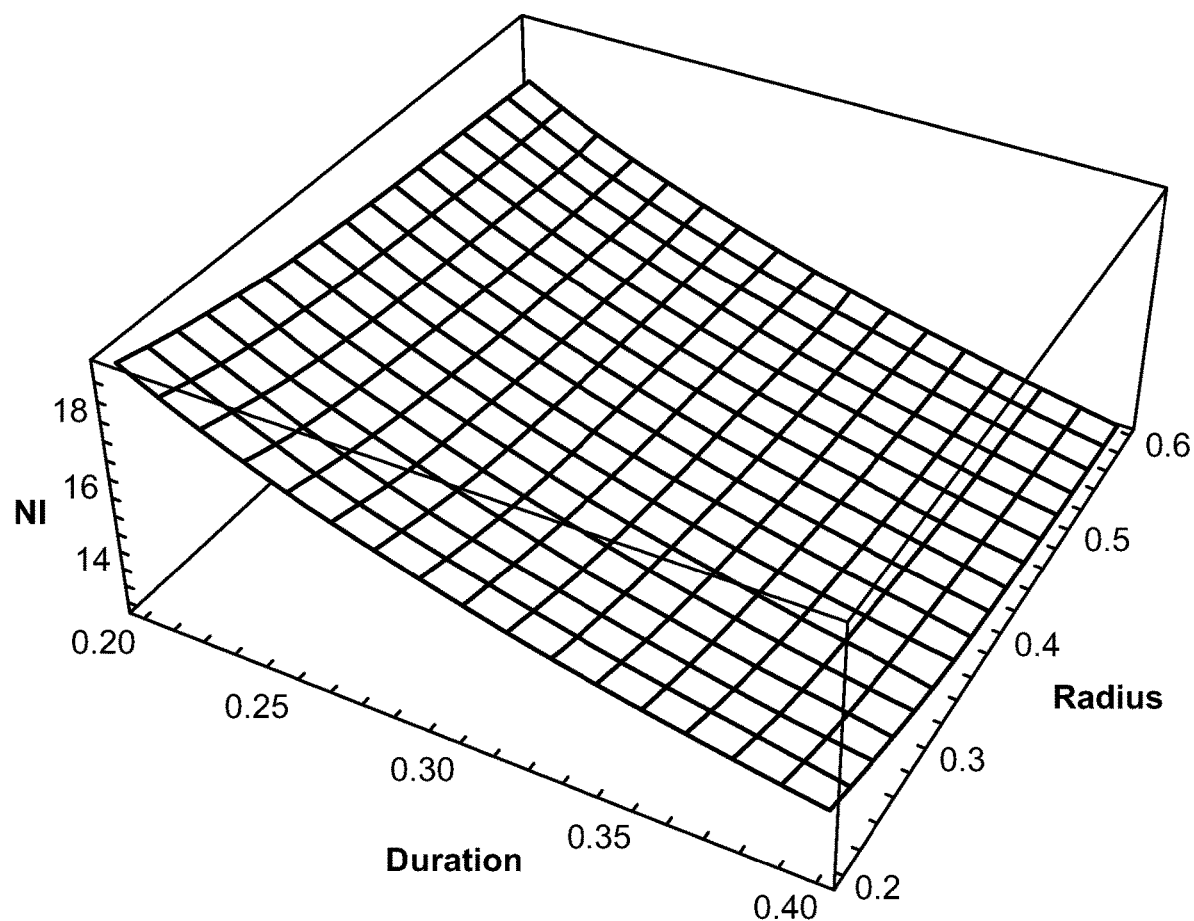
FIGS. 3-6 are graphs illustrating the peak ampere turns for various radiofrequencies, duty cycles, and coil radii.
Figure 4:
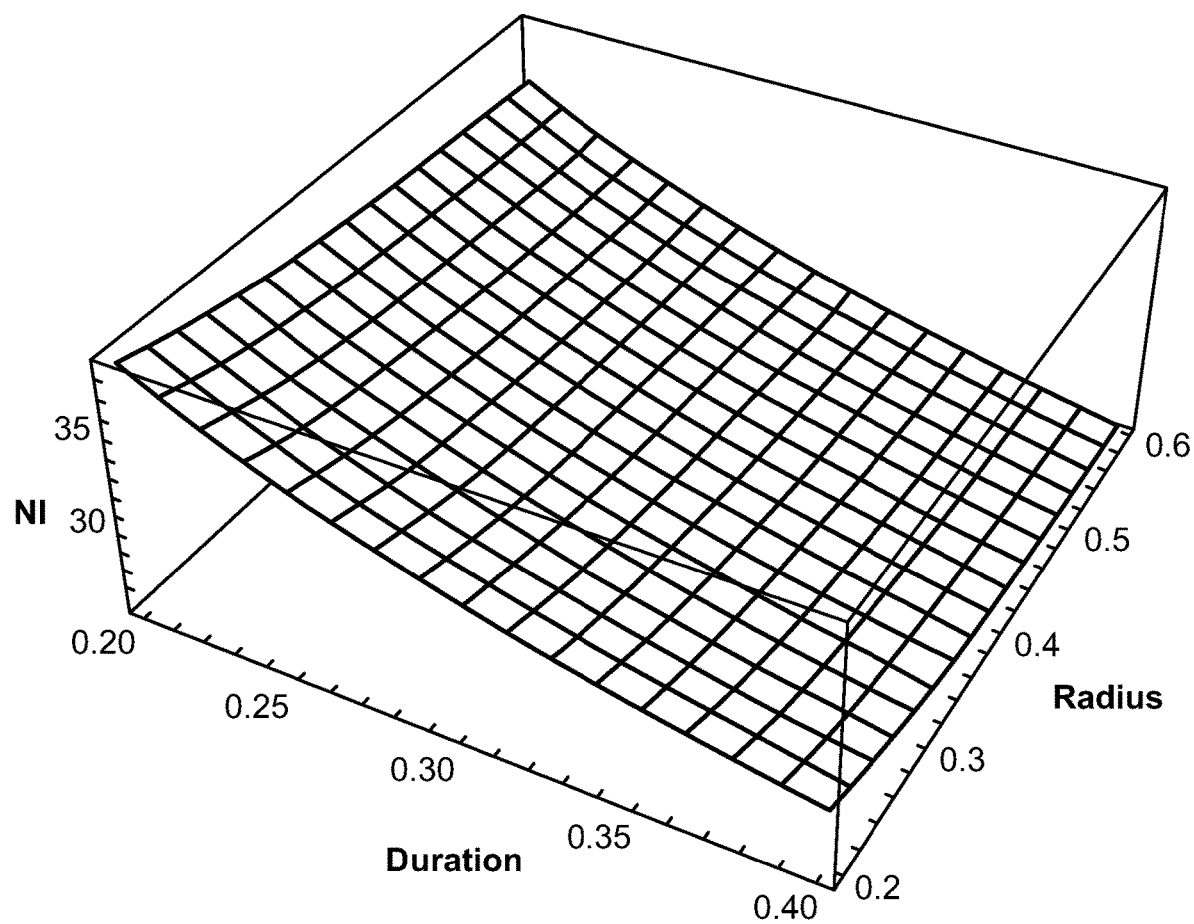
Figure 5:
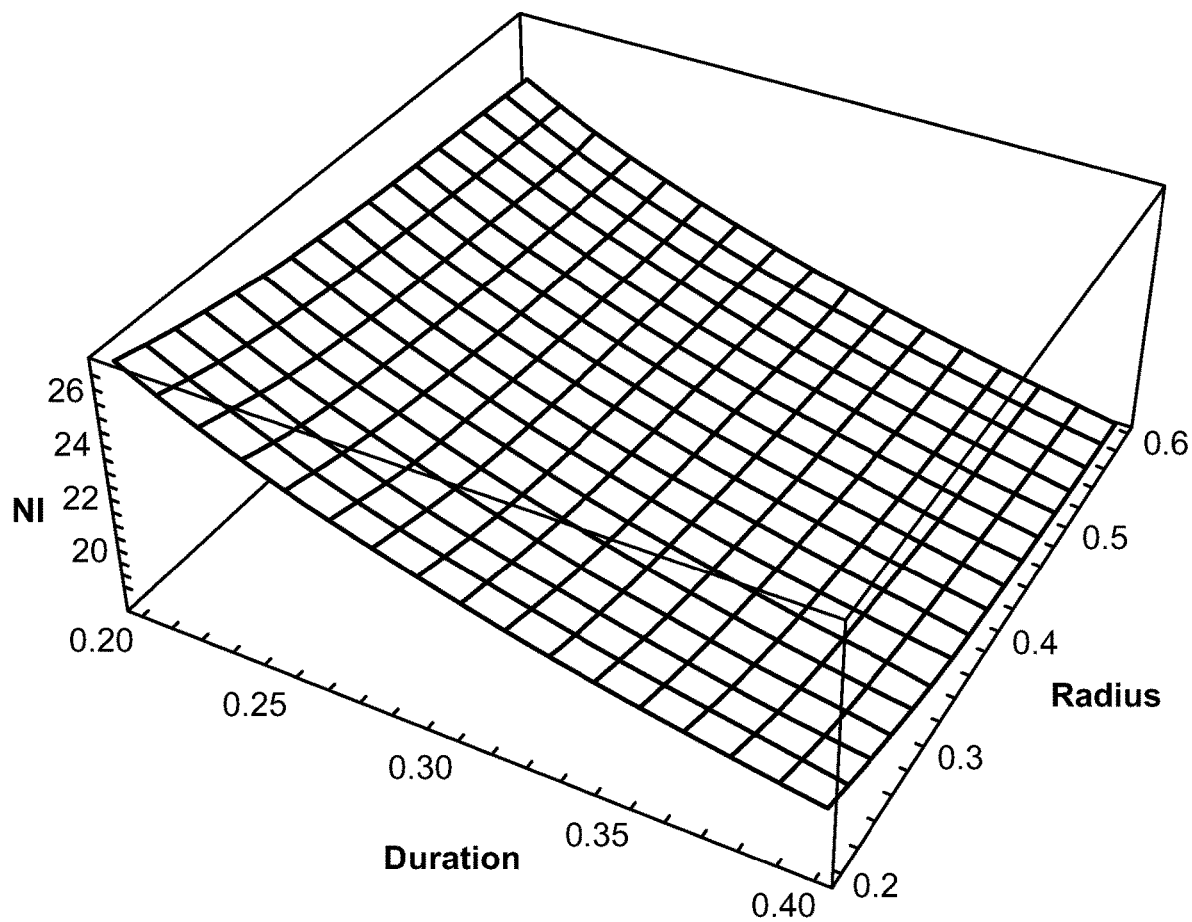
Figure 6:
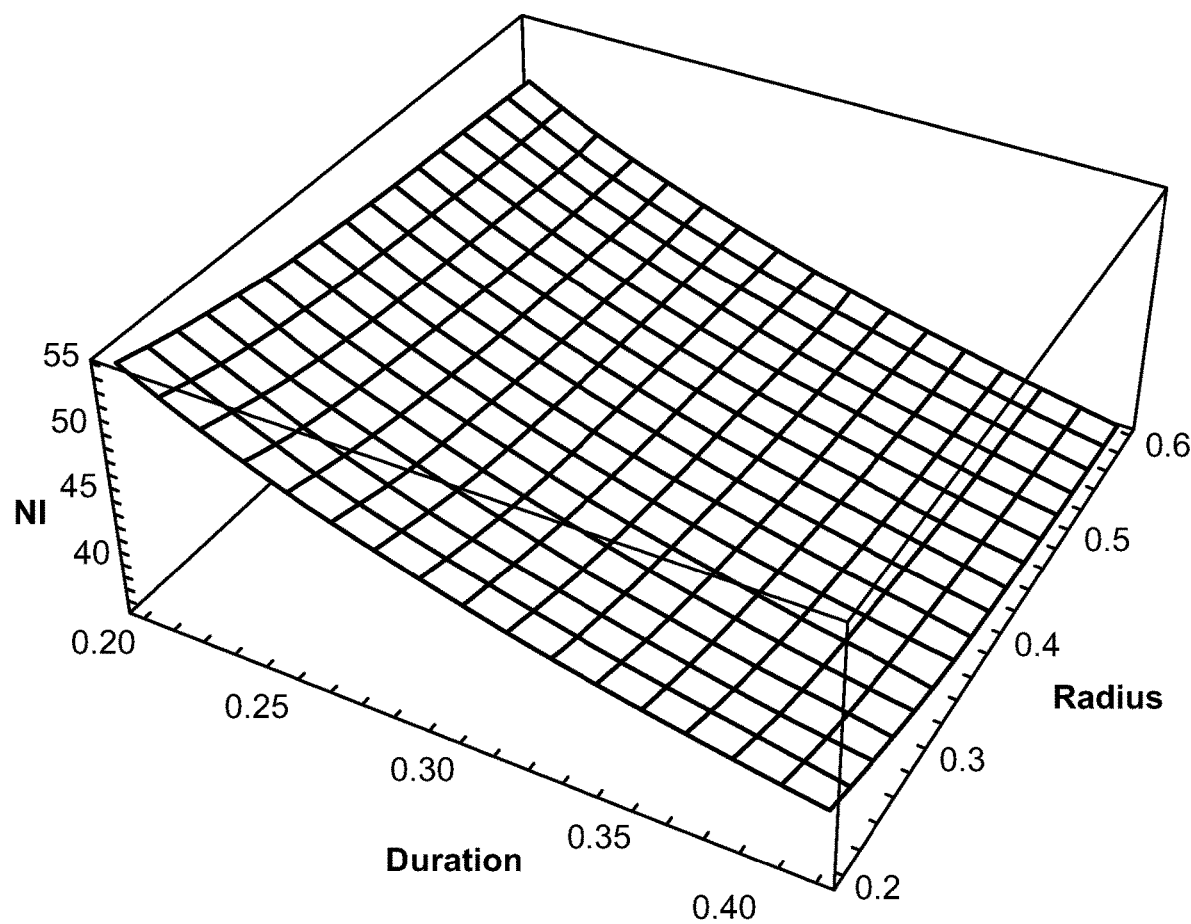

Preferred parameters for a radiofrequency energy source have been determined to be a coil radii between 2 and 6 mm, radiofrequencies in the range of 3-6 MHz, total pulse train durations of 0.2 to 0.4 seconds, and a duty cycle of between 2.5% and 5%. FIGS. 3-6 show how the number of ampere turns varies as these parameters are varied in order to give a temperature rise that produces an Arrhenius integral of approximately one or unity for HSP activation. With reference to FIG. 3, for an RF frequency of 6 MHz, a pulse train duration of between 0.2 and 0.4 seconds, a coil radius between 0.2 and 0.6 cm, and a duty cycle of 5%, the peak ampere turns (NI) is 13 at the 0.6 cm coil radius and 20 at the 0.2 cm coil radius. For a 3 MHz frequency, as illustrated in FIG. 4, the peak ampere turns is 26 when the pulse train duration is 0.4 seconds and the coil radius is 0.6 cm and the duty cycle is 5%. However, with the same 5% duty cycle, the peak ampere turns is 40 when the coil radius is 0.2 cm and the pulse train duration is 0.2 seconds. A duty cycle of 2.5% is used in FIGS. 5 and 6. This yields, as illustrated in FIG. 5, 18 amp turns for a 6 MHz radiofrequency having a coil radius of 0.6 cm and a pulse train duration of 0.4 seconds, and 29 amp turns when the coil radius is only 0.2 cm and the pulse train duration is 0.2 seconds. With reference to FIG. 6, with a duty cycle of 2.5% and a radiofrequency of 3 MHz, the peak ampere turns is 36 when the pulse train duration is 0.4 seconds and the coil radius is 0.6 cm, and 57 amp turns when the pulse train duration is 0.2 seconds and the coil radius is 0.2 cm.

Figure 7:
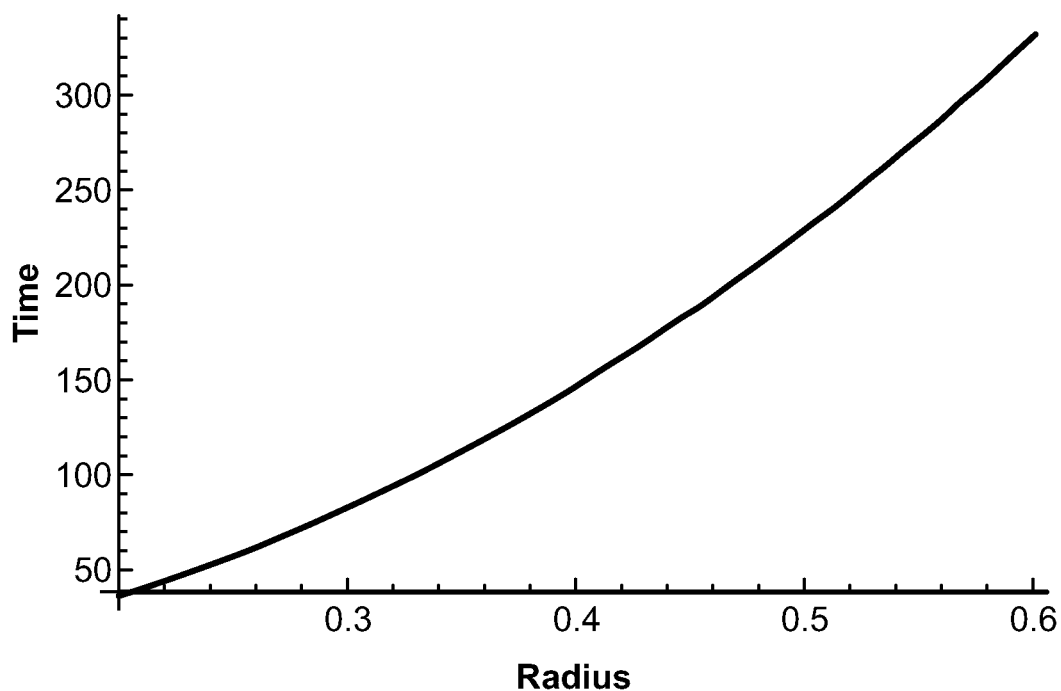
FIG. 7 is a graph depicting the time for temperature rise to decay compared to radiofrequency coil radius.

The time, in seconds, for the temperature rise to decay from approximately 10° C. to approximately 1° C. for coil radii between 0.2 cm and 0.6 cm is illustrated for a radiofrequency energy source in FIG. 7. The temperature decay time is approximately 37 seconds when the radiofrequency coil radius is 0.2 cm, and approximately 233 seconds when the radiofrequency coil radius is 0.5 cm. When the radiofrequency coil radius is 0.6 cm, the decay time is approximately 336 seconds, which is still within the acceptable range of decay time, but at an upper range thereof.

Microwaves are another electromagnetic energy source which can be utilized in accordance with the present invention. The frequency of the microwave determines the tissue penetration distance. The gain of a conical microwave horn is large compared to the microwave wavelength, indicating under those circumstances that the energy is radiated mostly in a narrow forward load. Typically, a microwave source used in accordance with the present invention has a linear dimension on the order of a centimeter or less, thus the source is smaller than the wavelength, in which case the microwave source can be approximated as a dipole antenna. Such small microwave sources are easier to insert into internal body cavities and can also be used to radiate external surfaces. In that case, the heated region can be approximated by a hemisphere with a radius equal to the absorption length of the microwave in the body tissue being treated. As the microwaves are used to treat tissue near external surfaces or surfaces accessible from internal cavities, frequencies in the 10-20 GHz range are used, wherein the corresponding penetration distances are only between approximately 2 and 4 mm.

The temperature rise of the tissue using a microwave energy source is determined by the average power of the microwave and the total pulse train duration. The duty cycle of the pulse train determines the peak power in a single pulse in a train of pulses. As the radius of the source is taken to be less than approximately 1 centimeter, and frequencies between 10 and 20 GHz are typically used, a resulting pulse train duration of 0.2 and 0.6 seconds is preferred.

The required power decreases monotonically as the train duration increases and as the microwave frequency increases. For a frequency of 10 GHz, the average power is 18 watts when the pulse train duration is 0.6 seconds, and 52 watts when the pulse train duration is 0.2 seconds. For a 20 GHz microwave frequency, an average power of 8 watts is used when the pulse train is 0.6 seconds, and can be 26 watts when the pulse train duration is only 0.2 seconds. The corresponding peak power are obtained from the average power simply by dividing by the duty cycle.

Figure 8:
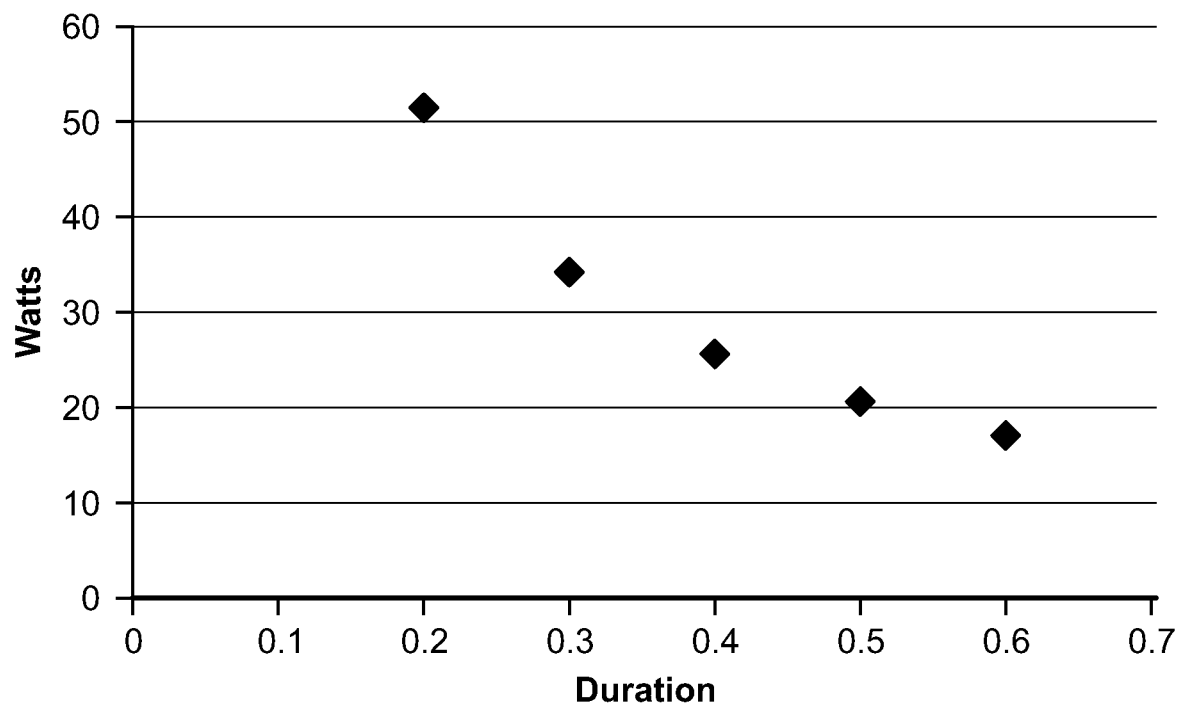
FIGS. 8 and 9 are graphs depicting the average microwave power compared to microwave frequency and pulse train durations.
Figure 9:
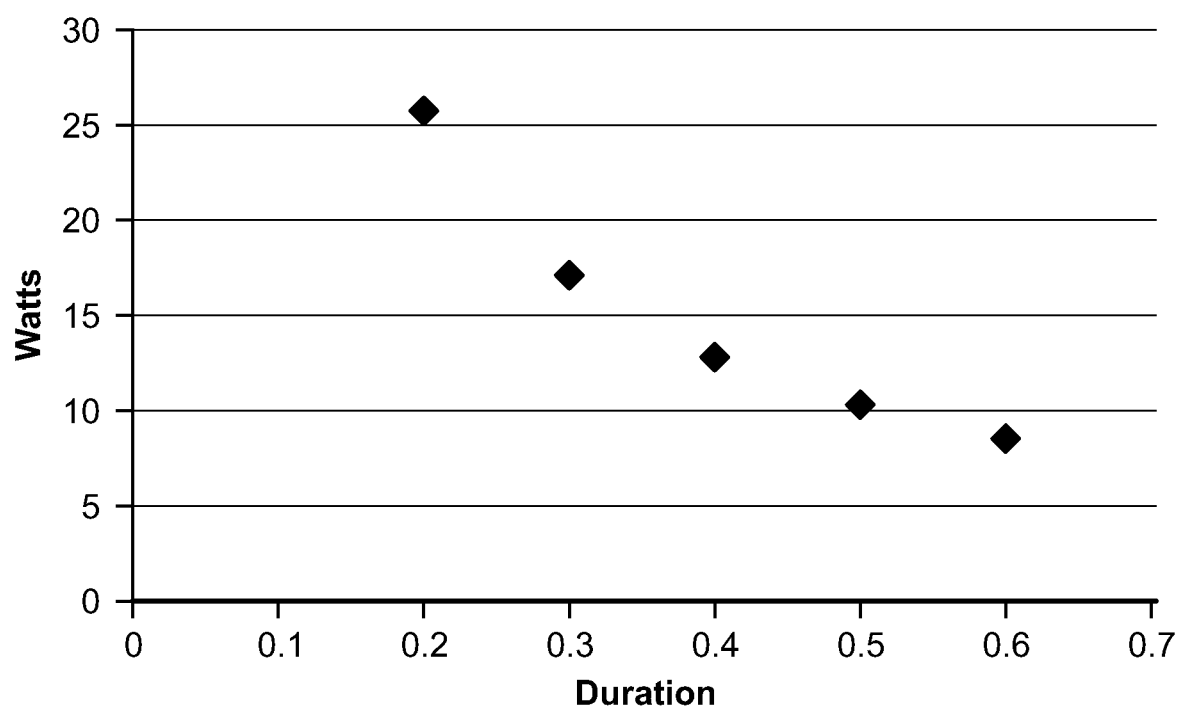

With reference now to FIG. 8, a graph depicts the average microwave power in watts of a microwave having a frequency of 10 GHz and a pulse train duration from between 0.2 seconds and 0.6 seconds. FIG. 9 is a similar graph, but showing the average microwave power for a microwave having a frequency of 20 GHz. Thus, it will be seen that the average microwave source power varies as the total train duration and microwave frequency vary. The governing condition, however, is that the Arrhenius integral for HSP activation in the heated region is approximately 1.

Figure 10:
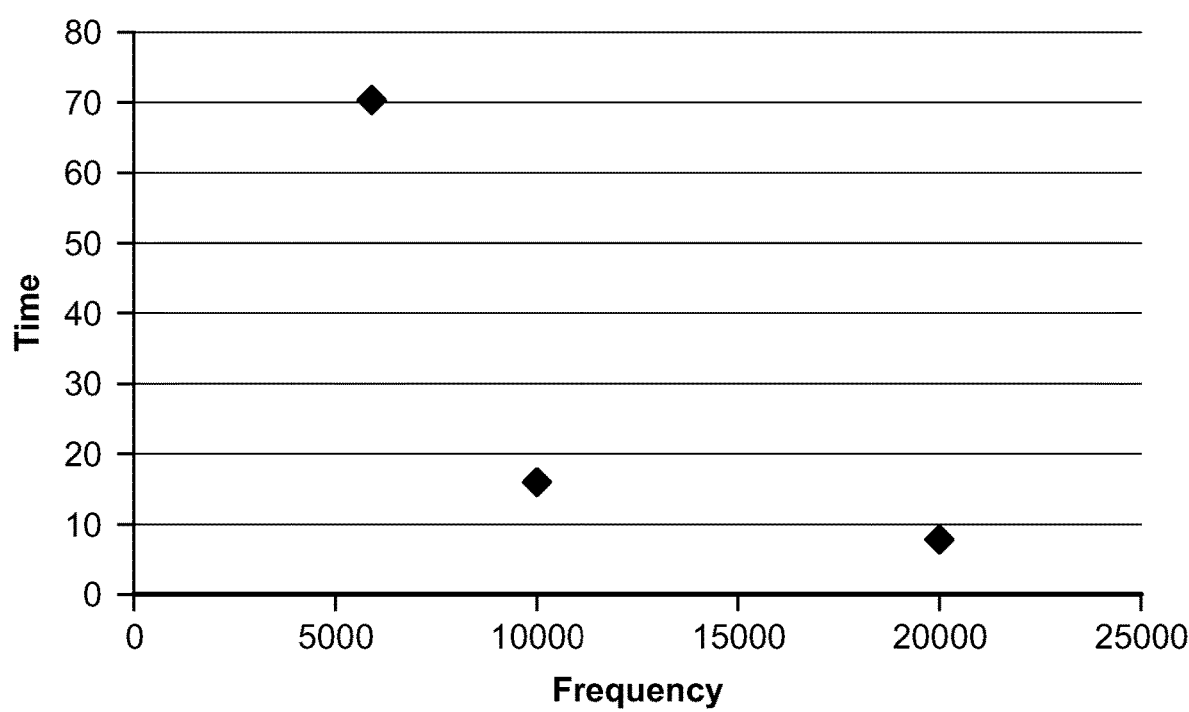
FIG. 10 is a graph depicting the time for the temperature to decay for various microwave frequencies.

With reference to FIG. 10, a graph illustrates the time, in seconds, for the temperature to decay from approximately 10° C. to 1° C. compared to microwave frequencies between 58 MHz and 20000 MHz. The minimum and maximum temperature decay for the preferred range of microwave frequencies are 8 seconds when the microwave frequency is 20 GHz, and 16 seconds when the microwave frequency is 10 GHz.

Utilizing ultrasound as an energy source enables heating of surface tissue, and tissues of varying depths in the body, including rather deep tissue. The absorption length of ultrasound in the body is rather long, as evidenced by its widespread use for imaging. Accordingly, ultrasound can be focused on target regions deep within the body, with the heating of a focused ultrasound beam concentrated mainly in the approximately cylindrical focal region of the beam. The heated region has a volume determined by the focal waist of the airy disc and the length of the focal waist region, that is the confocal parameter. Multiple beams from sources at different angles can also be used, the heating occurring at the overlapping focal regions.

For ultrasound, the relevant parameters for determining tissue temperature are frequency of the ultrasound, total train duration, and transducer power when the focal length and diameter of the ultrasound transducer is given. The frequency, focal length, and diameter determine the volume of the focal region where the ultrasound energy is concentrated. It is the focal volume that comprises the target volume of tissue for treatment. Transducers having a diameter of approximately 5 cm and having a focal length of approximately 10 cm are readily available. Favorable focal dimensions are achieved when the ultrasound frequency is between 1 and 5 MHz, and the total train duration is 0.1 to 0.5 seconds. For example, for a focal length of 10 cm and the transducer diameter of 5 cm, the focal volumes are 0.02 cc at 5 MHz and 2.36 cc at 1 MHz.

Figure 11:
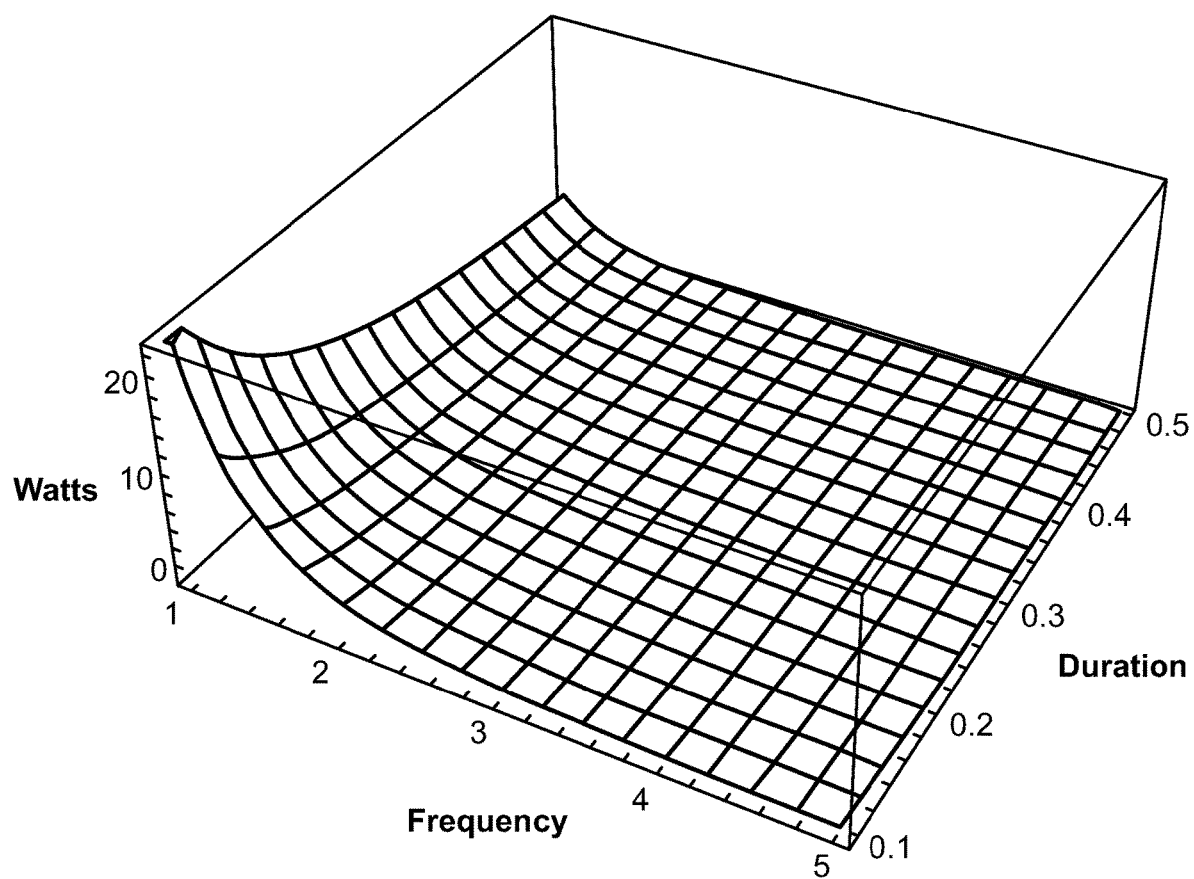
FIG. 11 is a graph depicting the average ultrasound source power compared to frequency and pulse train duration.

With reference now to FIG. 11, a graph illustrates the average source power in watts compared to the frequency (between 1 MHz and 5 MHz), and the pulse train duration (between 0.1 and 0.5 seconds). A transducer focal length of 10 cm and a source diameter of 5 cm have been assumed.

The required power to give the Arrhenius integral for HSP activation of approximately 1 decreases monotonically as the frequency increases and as the total train duration increases. Given the preferred parameters, the minimum power for a frequency of 1 GHz and a pulse train duration of 0.5 seconds is 5.72 watts, whereas for the 1 GHz frequency and a pulse train duration of 0.1 seconds the maximum power is 28.6 watts. For a 5 GHz frequency, 0.046 watts is required for a pulse train duration of 0.5 seconds, wherein 0.23 watts is required for a pulse train duration of 0.1 seconds. The corresponding peak power during an individual pulse is obtained simply by dividing by the duty cycle.

Figure 12:
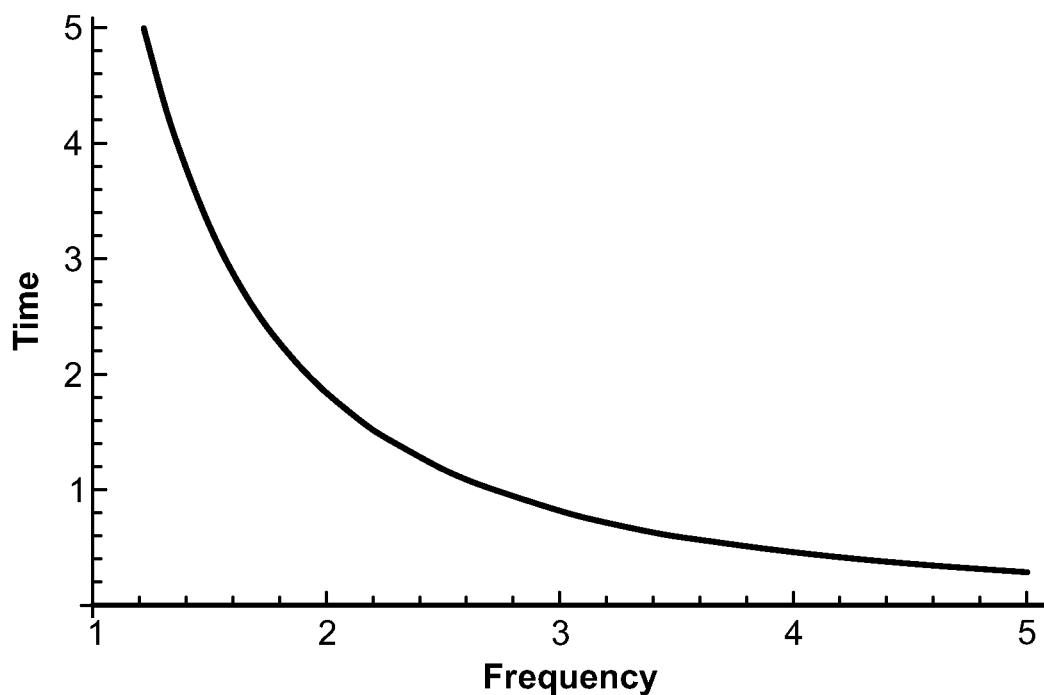
FIGS. 12 and 13 are graphs depicting the time for temperature decay for various ultrasound frequencies.
Figure 13:
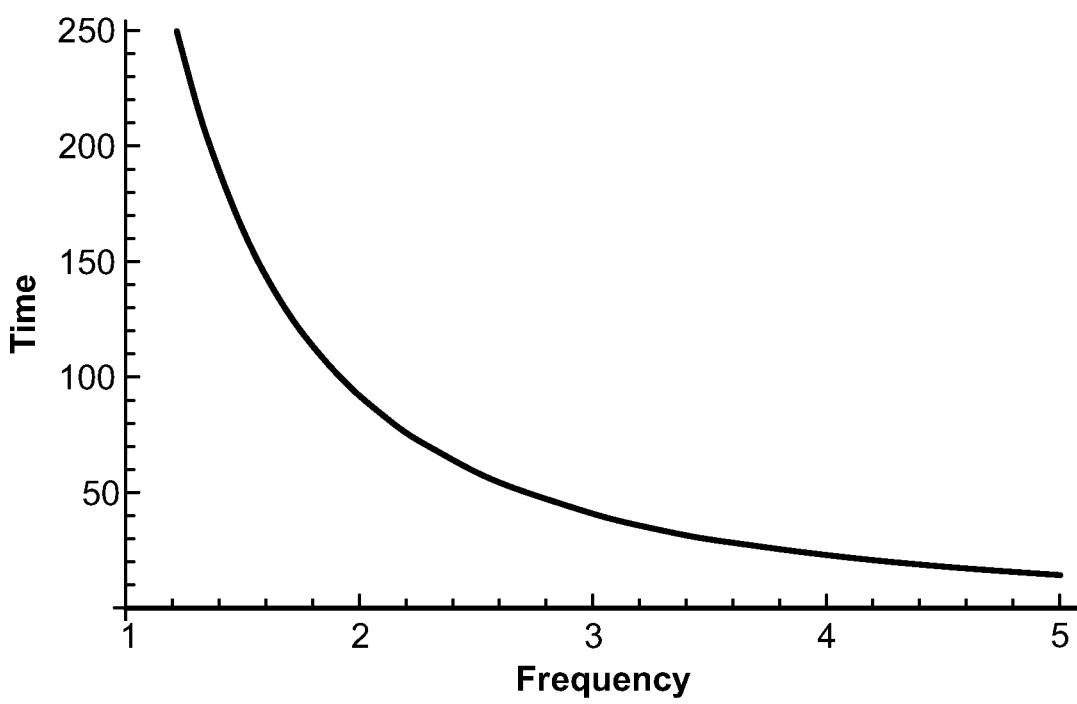

FIG. 12 illustrates the time, in seconds, for the temperature to diffuse or decay from 10° C. to 6° C. when the ultrasound frequency is between 1 and 5 MHz. FIG. 13 illustrates the time, in seconds, to decay from approximately 10° C. to approximately 1° C. for ultrasound frequencies from 1 to 5 MHz. For the preferred focal length of 10 cm and the transducer diameter of 5 cm, the maximum time for temperature decay is 366 seconds when the ultrasound frequency is 1 MHz, and the minimum temperature decay is 15 seconds when the microwave frequency is 5 MHz. As the FDA only requires the temperature rise be less than 6° C. for test times of minutes, the 366 second decay time at 1 MHz to get to a rise of 1° C. over the several minutes is allowable. As can be seen in FIGS. 12 and 13, the decay times to a rise of 6° C. are much smaller, by a factor of approximately 70, than that of 1° C.

Figure 14:
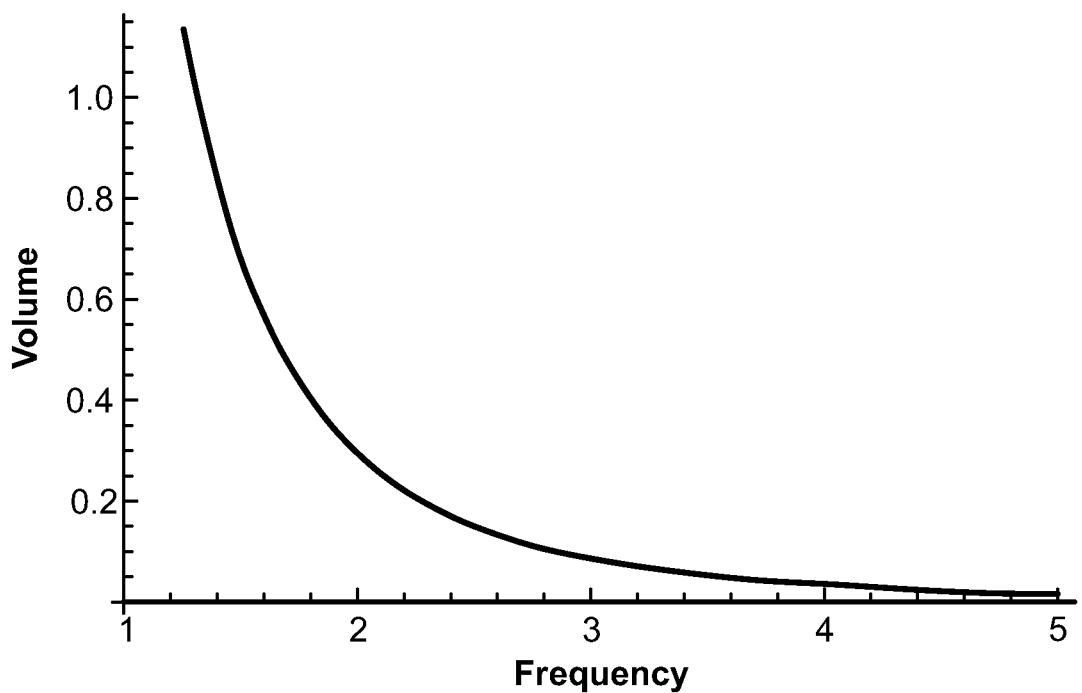
FIG. 14 is a graph depicting the volume of focal heated region compared to ultrasound frequency.

FIG. 14 illustrates the volume of focal heated region, in cubic centimeters, as compared to ultrasound frequencies from between 1 and 5 MHz. Considering ultrasound frequencies in the range of 1 to 5 MHz, the corresponding focal sizes for these frequencies range from 3.7 mm to 0.6 mm, and the length of the focal region ranges from 5.6 cm to 1.2 cm. The corresponding treatment volumes range from between approximately 2.4 cc and 0.02 cc.

Examples of parameters giving a desired HSP activation Arrhenius integral greater than 1 and damage Arrhenius integral less than 1 is a total ultrasound power between 5.8-17 watts, a pulse duration of 0.5 seconds, an interval between pulses of 5 seconds, with total number of pulses 10 within the total pulse stream time of 50 seconds. The target treatment volume would be approximately 1 mm on a side. Larger treatment volumes could be treatable by an ultrasound system similar to a laser diffracted optical system, by applying ultrasound in multiple simultaneously applied adjacent but separated and spaced columns. The multiple focused ultrasound beams converge on a very small treatment target within the body, the convergence allowing for a minimal heating except at the overlapping beams at the target. This area would be heated and stimulate the activation of HSPs and facilitate protein repair by transient high temperature spikes. However, given the pulsating aspect of the invention as well as the relatively small area being treated at any given time, the treatment is in compliance with FDA/FCC requirements for long term (minutes) average temperature rise <1K. An important distinction of the invention from existing therapeutic heating treatments for pain and muscle strain is that there are no high T spikes in existing techniques, and these are required for efficiently activating HSPs and facilitating protein repair to provide healing at the cellular level.

The pulse train mode of energy delivery has a distinct advantage over a single pulse or gradual mode of energy delivery, as far as the activation of remedial HSPs and the facilitation of protein repair is concerned. There are two considerations that enter into this advantage:

First, a big advantage for HSP activation and protein repair in an SDM energy delivery mode comes from producing a spike temperature of the order of 10° C. This large rise in temperature has a big impact on the Arrhenius integrals that describe quantitatively the number of HSPs that are activated and the rate of water diffusion into the proteins that facilitates protein repair. This is because the temperature enters into an exponential that has a big amplification effect.

It is important that the temperature rise not remain at the high value (10° C. or more) for long, because then it would violate the FDA and FCC requirements that over periods of minutes the average temperature rise must be less than 1° C. (or in the case of ultrasound 6° C.).

An SDM mode of energy delivery uniquely satisfies both of these foregoing considerations by judicious choice of the power, pulse time, pulse interval, and the volume of the target region to be treated. The volume of the treatment region enters because the temperature must decay from its high value of the order of 10° C. fairly rapidly in order for the long term average temperature rise not to exceed the long term FDA/FCC limit of 6° C. for ultrasound frequencies and 1° C. or less for electromagnetic radiation energy sources.

For a region of linear dimension L, the time that it takes the peak temperature to e-fold in tissue is roughly $L^2/16D$, where $D=0.00143$ cm$^2$/sec is the typical heat diffusion coefficient. For example, if $L=1$ mm, the decay time is roughly 0.4 sec. Accordingly, for a region 1 mm on a side, a train consisting of 10 pulses each of duration 0.5 seconds, with an interval between pulses of 5 second can achieve the desired momentary high rise in temperature while still not exceeding an average long term temperature rise of 1° C. This is demonstrated further below.

The limitation of heated volume is the reason why RF electromagnetic radiation is not as good of a choice for SDM-type treatment of regions deep with the body as ultrasound. The long skin depths (penetration distances) and Ohmic heating all along the skin depth results in a large heated volume whose thermal inertia does not allow both the attainment of a high spike temperature that activates HSPs and facilitates protein repair, and the rapid temperature decay that satisfies the long term FDA and FCC limit on average temperature rise.

Ultrasound has already been used to therapeutically heat regions of the body to ease pain and muscle strain. However, the heating has not followed the SDM-type protocol and does not have the temperature spikes that are responsible for the excitation of HSPs.

Consider, then, a group of focused ultrasound beams that are directed at a target region deep within the body. To simplify the mathematics, suppose that the beams are replaced by a single source with a spherical surface shape that is focused on the center of the sphere. The absorption lengths of ultrasound can be fairly long. Table 3 below shows typical absorption coefficients for ultrasound at 1 MHz. The absorption coefficients are roughly proportional to the frequency.

TABLE 3

Typical absorption coefficients for 1 MHz ultrasound in body tissue:

| Body Tissue | Attenuation Coefficient at 1 MHz (cm$^{-1}$) |
|---|---|
| Water | 0.00046 |
| Blood | 0.0415 |
| Fat | 0.145 |
| Liver | 0.115-0.217 |
| Kidney | 0.23 |

TABLE 3-continued

Typical absorption coefficients for 1 MHz ultrasound in body tissue:

| Body Tissue | Attenuation Coefficient at 1 MHz (cm$^{-1}$) |
|---|---|
| Muscle | 0.3-0.76 |
| Bone | 1.15 |

Assuming that the geometric variation of the incoming radiation due to the focusing dominates any variation due to attenuation, the intensity of the incoming ultrasound at a distance r from the focus can be written approximately as:

$$I(r)=P/(4\pi r^2) \qquad [1]$$

where P denotes the total ultrasound power.

The temperature rise at the end of a short pulse of duration $t_p$ at r is then $$dT(t_p)=P\alpha t_p/(4\pi C_v r^2) \qquad [2]$$

where $\alpha$ is the absorption coefficient and $C_v$ is the specific volume heat capacity. This will be the case until the r is reached at which the heat diffusion length at $t_p$ becomes comparable to r, or the diffraction limit of the focused beam is reached. For smaller r, the temperature rise is essentially independent of r. As an example, suppose the diffraction limit is reached at a radial distance that is smaller than that determined by heat diffusion. Then $$r_{dif}=(4Dt_p)^{1/2} \qquad [3]$$

where D is the heat diffusion coefficient, and for $r<r_{dif}$ the temperature rise at $t_p$ is $$dT(r_{dif},t_p)=3P\alpha/(8\pi C_v D) \text{ when } r<rd_{if} \qquad [4]$$

Thus, at the end of the pulse, we can write for the temperature rise:

$$dT_p(r)=\{P\alpha t_p/(4\pi C_v)\}[(6/r_{dif}^2)U\{r_{dif}-r\}+(1/r^2)U(r-r_{dif})] \qquad [5]$$

On applying the Green's function for the heat diffusion equation, $$G(r,t)=(4\Omega Dt)^{-3/2}\exp[-r^2/(4Dt)] \qquad [6]$$

to this initial temperature distribution, we find that the temperature dT(t) at the focal point r=0 at a time t is $$dT(t)=[dT_o/\{(1/2)+(\pi^{1/2}/6)\}][(1/2)(t_p/t)^{3/2}+(\pi^{1/2}/6)(t_p/t)] \qquad [7]$$

with $$dT_o=3P\alpha/(8\pi C_v D) \qquad [8]$$

Figure 15:
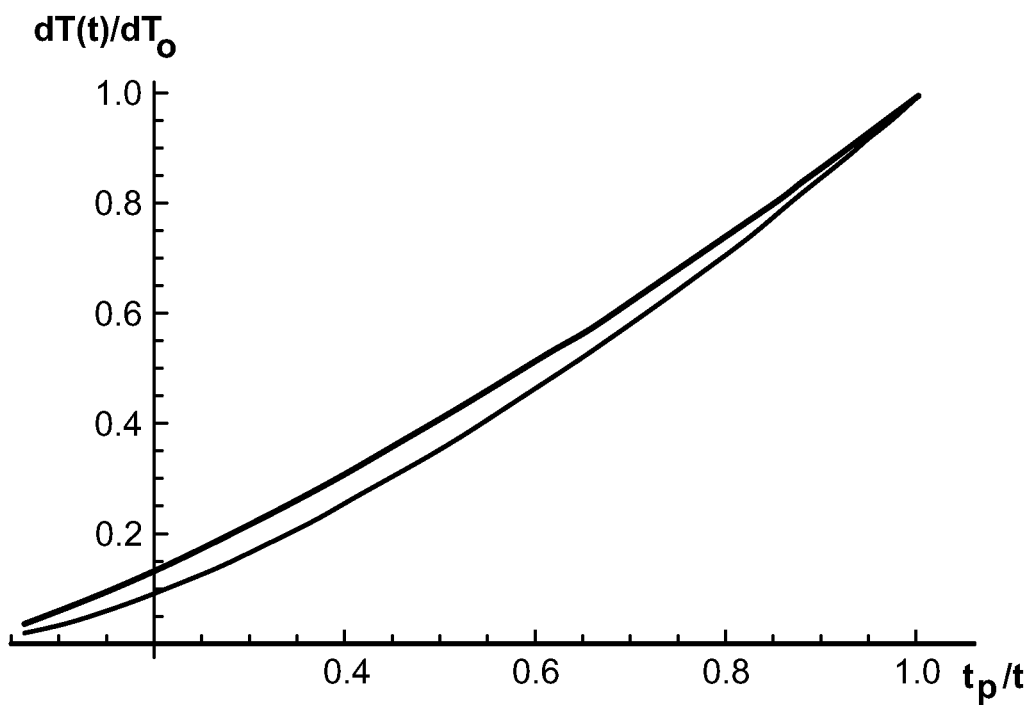
FIG. 15 is a graph comparing equations for temperature over pulse durations for an ultrasound energy source.

A good approximation to eq. [7] is provided by:

$$dT(t)\approx dT_o(t_p/t)^{3/2} \qquad [9]$$

as can be seen in FIG. 15, which is a comparison of eqs. [7] and [9] for $dT(t)/dT_o$ at the target treatment zone. The bottom curve is the approximate expression of eq [9].

The Arrhenius integral for a train of N pulses can now be evaluated with the temperature rise given by eq. [9]. In this expression, $$dT_N(t)=\Sigma dT(t-nt_I) \qquad [11]$$

where $dT(t-nt_I)$ is the expression of eq. [9] with t replaced by $t-nt_I$ and with $t_I$ designating the interval between pulses.

The Arrhenius integral can be evaluated approximately by dividing the integration interval into the portion where the temperature spikes occur and the portion where the temperature spike is absent. The summation over the temperature spike contribution can be simplified by applying Laplace's end point formula to the integral over the temperature spike. In addition, the integral over the portion when the spikes are absent can be simplified by noting that the non-spike temperature rise very rapidly reaches an asymptotic value, so that a good approximation is obtained by replacing the varying time rise by its asymptotic value. When these approximations are made, eq. [10] becomes:

$$\Omega = AN[\{t_p(2k_B T_o^2/(3EdT_o)\}\exp[-(E/k_B)1/(T_o+dT_o+dT_N(Nt_l))]+\exp[-(E/k_B)1/(T_o+dT_N(Nt_l))]] \quad [12]$$

where $$dT_N(Nt_l) \approx 2.5 dT_o(t_p/t_l)^{3/2} \quad [13]$$

(The 2.5 in eq. [13] arises from the summation over n of $(N-n)^{-3/2}$ and is the magnitude of the harmonic number (N,3/2) for typical N of interest.)

It is interesting to compare this expression with that for SDM applied to the retina. The first term is very similar to that from the spike contribution in the retina case, except that the effective spike interval is reduced by a factor of 3 for this 3D converging beam case. The second term, involving $dT_N(Nt_l)$ is much smaller than in the retina case. There the background temperature rise was comparable in magnitude to the spike temperature rise. But here in the converging beam case, the background temperature rise is much smaller by the ratio $(t_p/t_l)^{3/2}$. This points up the importance of the spike contribution to the activation or production of HSP's and the facilitation of protein repair, as the background temperature rise which is similar to the rise in a continuous ultrasound heating case is insignificant compared to the spike contribution. At the end of the pulse train, even this low background temperature rise rapidly disappears by heat diffusion.

Figure 16:
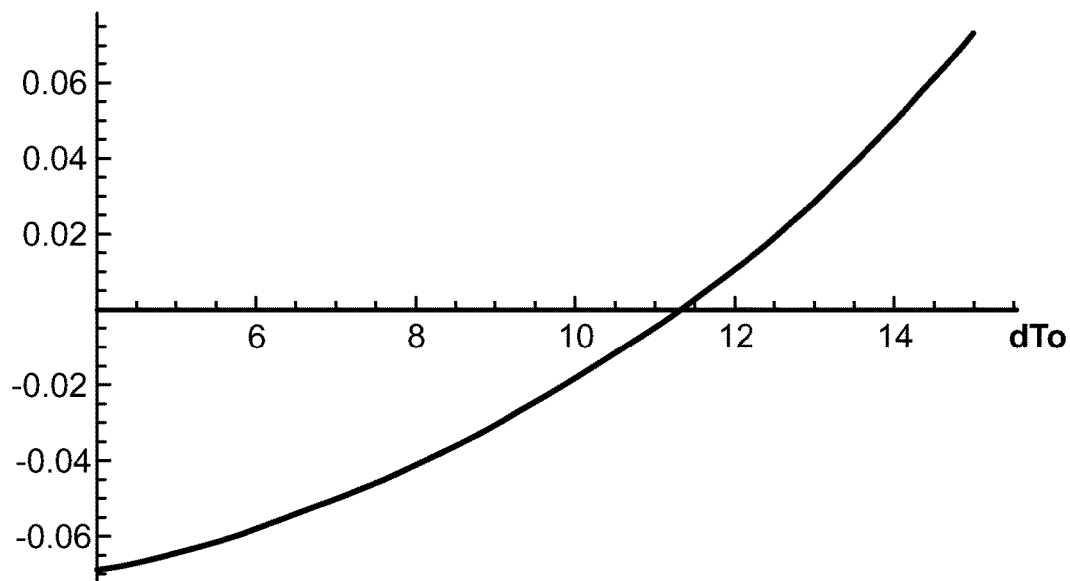
FIGS. 16 and 17 are graphs illustrating the magnitude of the logarithm of damage and HSP activation Arrhenius integrals as a function of temperature and pulse duration.
Figure 17:
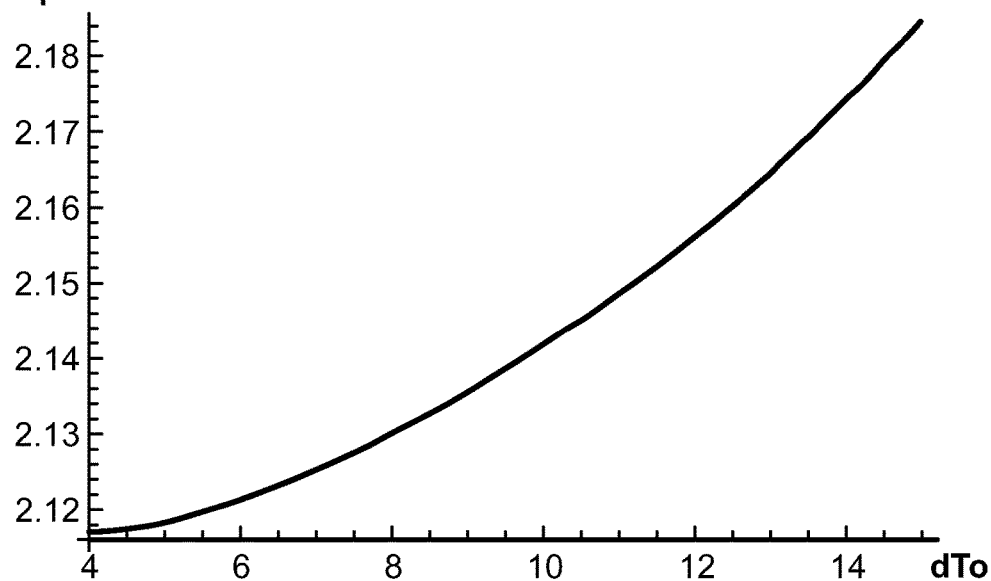

FIGS. 16 and 17 show the magnitude of the logarithm of the Arrhenius integrals for damage and for HSP activation or production as a function of $dT_o$ for a pulse duration $t_o=0.5$ sec, pulse interval $t_l=10$ sec, and total number of pulses N=10. Logarithm of Arrhenius integrals [eq. 12] for damage and for HSP activation as a function of the temperature rise in degrees Kelvin from a single pulse $dT_o$, for a pulse duration $t_o=0.5$ sec., pulse interval $t_l=10$ sec., and a total number of ultrasound pulses N=10. FIG. 16 shows the logarithm of the damage integral with the Arrhenius constants $A=8.71\times10^{33}$ sec$^{-1}$ and $E=3.55\times10^{-12}$ ergs. FIG. 17 shows the logarithm of the HSP activation integral with the Arrhenius constants $A=1.24\times10^{27}$ sec$^{-1}$ and $E=2.66\times10^{-12}$ ergs. The graphs in FIGS. 16 and 17 show that $\Omega_{damage}$ does not exceed 1 until $dT_o$ exceeds 11.3 K, whereas $\Omega_{hsp}$ is greater than 1 over the whole interval shown, the desired condition for cellular repair without damage.

Equation [8] shows that when $\alpha=0.1$ cm$^{-1}$, a $dT_o$ of 11.5 K can be achieved with a total ultrasound power of 5.8 watts. This is easily achievable. If a is increased by a factor of 2 or 3, the resulting power is still easily achievable. The volume of the region where the temperature rise is constant (i.e. the volume corresponding to $r=r_d=(4Dt_p)^{1/2}$) is 0.00064 cc. This corresponds to a cube that is 0.86 mm on a side.

This simple example demonstrates that focused ultrasound should be usable to stimulate reparative HSP's deep in the body with easily attainable equipment:

| | |
|---|---|
| Total ultrasound power: | 5.8 watts-17 watts |
| Pulse time | 0.5 sec |
| Pulse interval | 5 sec |
| Total train duration (N = 10) | 50 sec |

To expedite the treatment of larger internal volumes, a SAPRA system can be used.

The pulsed energy source may be directed to an exterior of a body which is adjacent to the target tissue or has a blood supply close to the surface of the exterior of the body. Alternatively, a device may be inserted into a cavity of a body to apply the pulsed energy source to the target tissue. Whether the energy source is applied outside of the body or inside of the body and what type of device is utilized depends upon the energy source selected and used to treat the target tissue.

Photostimulation, in accordance with the present invention, can be effectively transmitted to an internal surface area or tissue of the body utilizing an endoscope, such as a bronchoscope, proctoscope, colonoscope or the like. Each of these consist essentially of a flexible tube that itself contains one or more internal tubes. Typically, one of the internal tubes comprises a light pipe or multi-mode optical fiber which conducts light down the scope to illuminate the region of interest and enable the doctor to see what is at the illuminated end. Another internal tube could consist of wires that carry an electrical current to enable the doctor to cauterize the illuminated tissue. Yet another internal tube might consist of a biopsy tool that would enable the doctor to snip off and hold on to any of the illuminated tissue.

Figure 18:
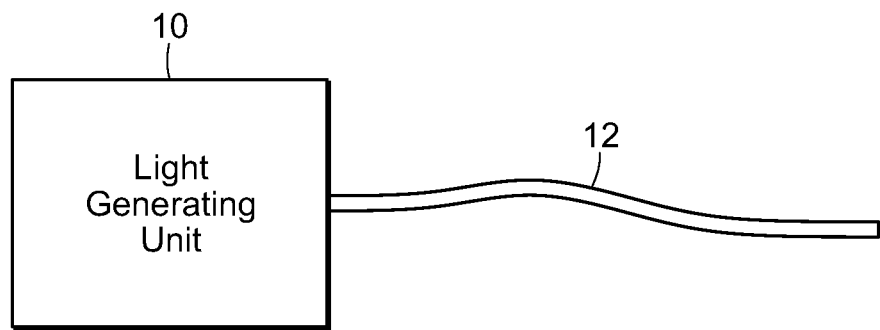
FIG. 18 is a diagrammatic view of a light generating unit that produces timed series of pulses, having a light pipe extending therefrom, in accordance with the present invention.
Figure 19:
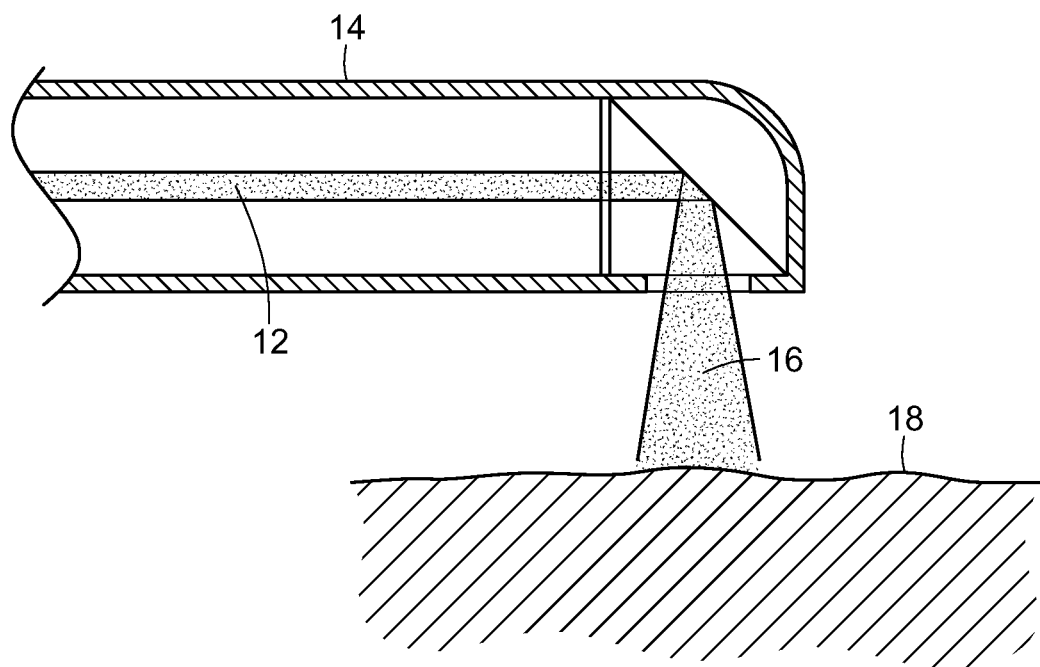
FIG. 19 is a cross-sectional view of a photostimulation delivery device delivering electromagnetic energy to target tissue, in accordance with the present invention.

In the present invention, one of these internal tubes is used as an electromagnetic radiation pipe, such as a multi-mode optical fiber, to transmit the SDM or other electromagnetic radiation pulses that are fed into the scope at the end that the doctor holds. With reference now to FIG. 18, a light generating unit 10, such as a laser having a desired wavelength and/or frequency is used to generate electromagnetic radiation, such as laser light, in a controlled, pulsed manner to be delivered through a light tube or pipe 12 to a distal end of the scope 14, illustrated in FIG. 19, which is inserted into the body and the laser light or other radiation 16 delivered to the target tissue 18 to be treated.

Figure 20:
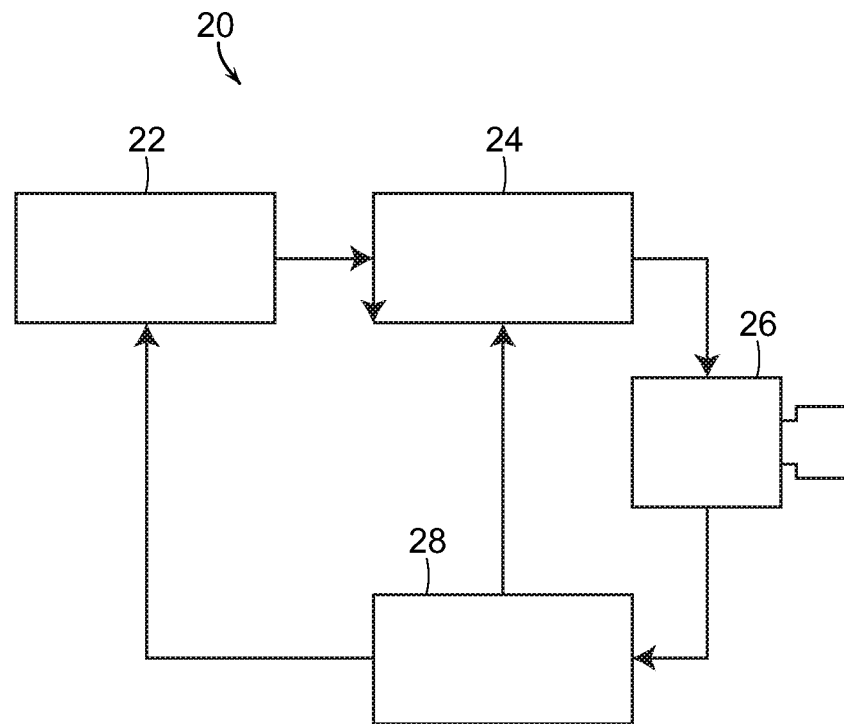
FIG. 20 is a diagrammatic view illustrating a system used to generate a laser light beam, in accordance with the present invention.

With reference now to FIG. 20, a schematic diagram is shown of a system for generating electromagnetic energy radiation, such as laser light, including SDM. The system, generally referred to by the reference number 20, includes a laser console 22, such as for example the 810 nm near infrared micropulsed diode laser in the preferred embodiment. The laser generates a laser light beam which is passed through optics, such as an optical lens or mask, or a plurality of optical lenses and/or masks 24 as needed. The laser projector optics 24 pass the shaped light beam to a delivery device 26, such as an endoscope, for projecting the laser beam light onto the target tissue of the patient. It will be understood that the box labeled 26 can represent both the laser beam projector or delivery device as well as a viewing system/camera, such as an endoscope, or comprise two different components in use. The viewing system/camera 26 provides feedback to a display monitor 28, which may also include the necessary computerized hardware, data input and controls, etc. for manipulating the laser 22, the optics 24, and/or the projection/viewing components 26.

Figure 21:
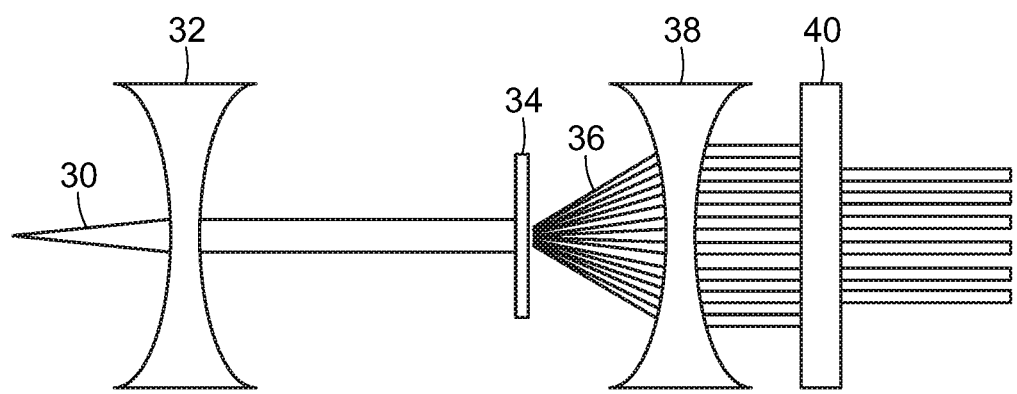
FIG. 21 is a diagrammatic view of optics used to generate a laser light geometric pattern, in accordance with the present invention.

With reference now to FIG. 21, in one embodiment, the laser light beam 30 may be passed through a collimator lens 32 and then through a mask 34. In a particularly preferred embodiment, the mask 34 comprises a diffraction grating. The mask/diffraction grating 34 produces a geometric object, or more typically a geometric pattern of simultaneously produced multiple laser spots or other geometric objects. This is represented by the multiple laser light beams labeled with reference number 36. Alternatively, the multiple laser spots may be generated by a plurality of fiber optic waveguides. Either method of generating laser spots allows for the creation of a very large number of laser spots simultaneously over a very wide treatment field. In fact, a very high number of laser spots, perhaps numbering in the hundreds even thousands or more could be simultaneously generated to cover a given area of the target tissue, or possibly even the entirety of the target tissue. A wide array of simultaneously applied small separated laser spot applications may be desirable as such avoids certain disadvantages and treatment risks known to be associated with large laser spot applications.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements.

The laser light passing through the mask 34 diffracts, producing a periodic pattern a distance away from the mask 34, shown by the laser beams labeled 36 in FIG. 21. The single laser beam 30 has thus been formed into hundreds or even thousands of individual laser beams 36 so as to create the desired pattern of spots or other geometric objects. These laser beams 36 may be passed through additional lenses, collimators, etc. 38 and 40 in order to convey the laser beams and form the desired pattern. Such additional lenses, collimators, etc. 38 and 40 can further transform and redirect the laser beams 36 as needed.

Arbitrary patterns can be constructed by controlling the shape, spacing and pattern of the optical mask 34. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Figure 22:
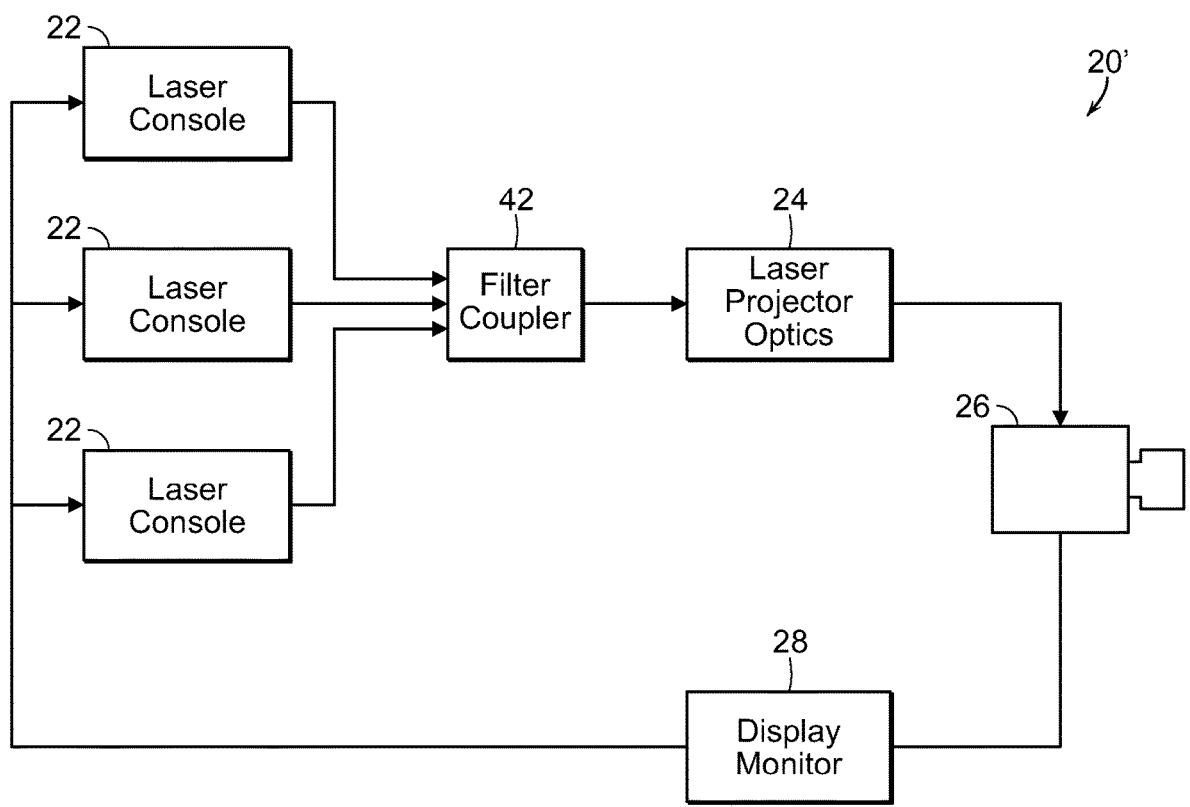
FIG. 22 is a diagrammatic view illustrating an alternate embodiment of the system used to generate laser light beams for treating tissue, in accordance with the present invention.

FIG. 22 illustrates diagrammatically a system which couples multiple light sources into the pattern-generating optical subassembly described above. Specifically, this system 20' is similar to the system 20 described in FIG. 20 above. The primary differences between the alternate system 20' and the earlier described system 20 is the inclusion of a plurality of laser consoles, the outputs of which are each fed into a fiber coupler 42. The fiber coupler produces a single output that is passed into the laser projector optics 24 as described in the earlier system. The coupling of the plurality of laser consoles 22 into a single optical fiber is achieved with a fiber coupler 42 as is known in the art. Other known mechanisms for combining multiple light sources are available and may be used to replace the fiber coupler described herein.

In this system 20' the multiple light sources 22 follow a similar path as described in the earlier system 20, i.e., collimated, diffracted, recollimated, and directed to the projector device and/or tissue. In this alternate system 20' the diffractive element must function differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the projector device 26 to the tissue for treatment.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the tissue, the application of the other wavelengths achieves either incomplete or overlapping coverage of the tissue. The second mode sequentially applies each light source of a varying wavelength with the proper steering pattern to achieve complete coverage of the tissue for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 23:
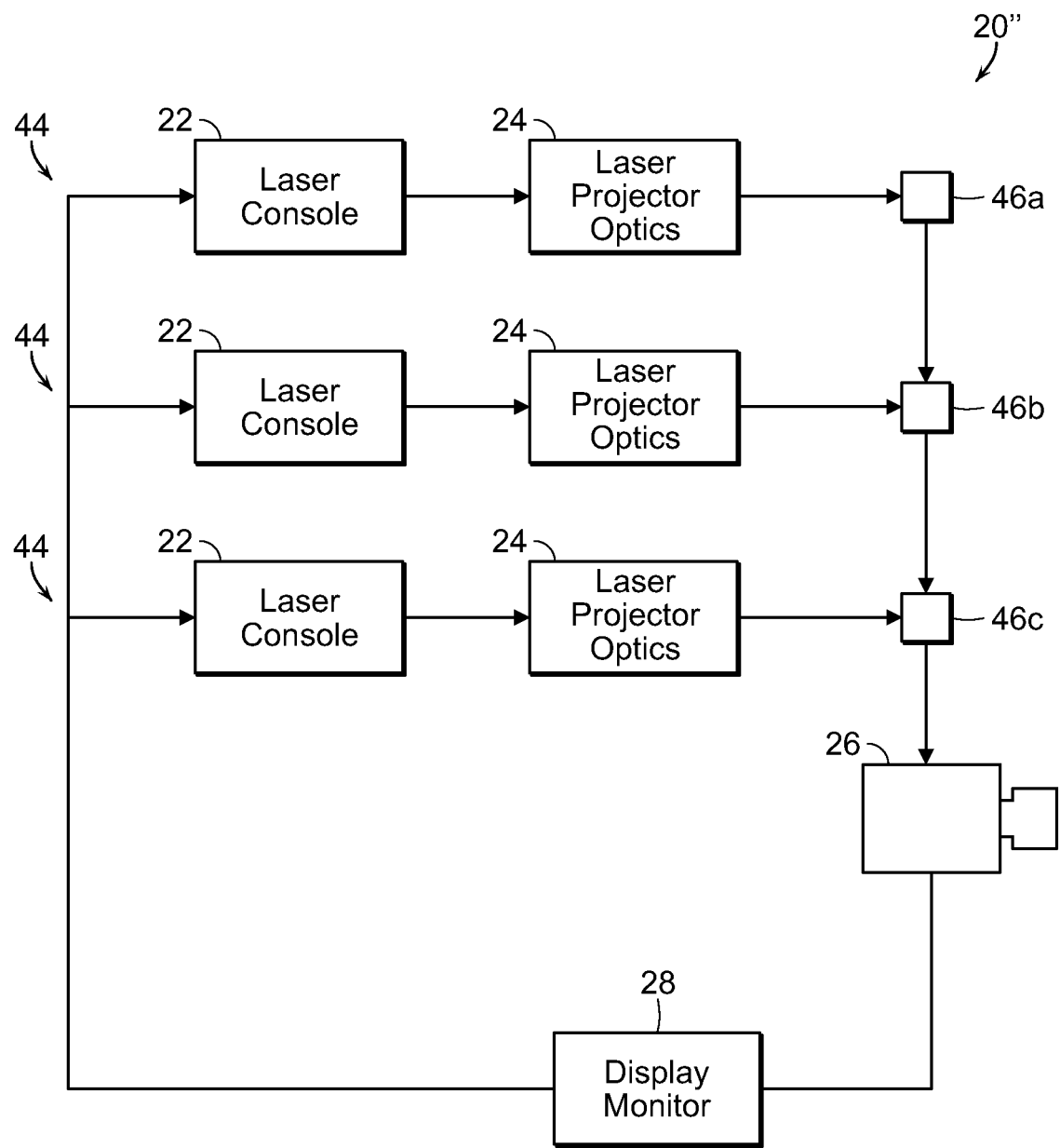
FIG. 23 is a diagrammatic view illustrating yet another embodiment of a system used to generate laser light beams to treat tissue in accordance with the present invention.

FIG. 23 illustrates diagrammatically yet another alternate embodiment of the inventive system 20". This system 20" is configured generally the same as the system 20 depicted in FIG. 20. The main difference resides in the inclusion of multiple pattern-generating subassembly channels tuned to a specific wavelength of the light source. Multiple laser consoles 22 are arranged in parallel with each one leading directly into its own laser projector optics 24. The laser projector optics of each channel 44a, 44b, 44c comprise a collimator 32, mask or diffraction grating 34 and recollimators 38, 40 as described in connection with FIG. 21 above—the entire set of optics tuned for the specific wavelength generated by the corresponding laser console 22. The output from each set of optics 24 is then directed to a beam splitter 46 for combination with the other wavelengths. It is known by those skilled in the art that a beam splitter used in reverse can be used to combine multiple beams of light into a single output. The combined channel output from the final beam splitter 46c is then directed through the projector device 26.

In this system 20" the optical elements for each channel are tuned to produce the exact specified pattern for that channel's wavelength. Consequently, when all channels are combined and properly aligned a single steering pattern may be used to achieve complete coverage of the tissue for all wavelengths.

The system 20" may use as many channels 44a, 44b, 44c, etc. and beam splitters 46a, 46b, 46c, etc. as there are wavelengths of light being used in the treatment.

Implementation of the system 20" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 20", each channel begins with a light source 22, which could be from an optical fiber as in other embodiments of the pattern-generating subassembly. This light source 22 is directed to the optical assembly 24 for collimation, diffraction, recollimation and directed into the beam splitter which combines the channel with the main output.

It will be understood that the laser light generating systems illustrated in FIGS. 20-23 are exemplary. Other devices and systems can be utilized to generate a source of SDM laser light which can be operably passed through to a projector device, typically in the form of an endoscope having a light pipe or the like. Other forms of electromagnetic radiation may also be generated and used, including ultraviolet waves, microwaves, other radiofrequency waves, and laser light at predetermined wavelengths. Moreover, ultrasound waves may also be generated and used to create a thermal time-course temperature spike in the target tissue sufficient to activate or produce heat shock proteins in the cells of the target tissue without damaging the target tissue itself. In order to do so, typically, a pulsed source of ultrasound or electromagnetic radiation energy is provided and applied to the target tissue in a manner which raises the target tissue temperature, such as between 6° C. and 11° C., transiently while only 6° C. or 1° C. or less for the long term, such as over several minutes.

For deep tissue that is not near an internal orifice, a light pipe is not an effective means of delivering the pulsed energy. In that case, pulsed low frequency electromagnetic energy or preferably pulsed ultrasound can be used to cause a series of temperature spikes in the target tissue.

Thus, in accordance with the present invention, a source of pulsed ultrasound or electromagnetic radiation is applied to the target tissue in order to stimulate HSP production or activation and to facilitate protein repair in the living animal tissue. In general, electromagnetic radiation may be ultraviolet waves, microwaves, other radiofrequency waves, laser light at predetermined wavelengths, etc. On the other hand, if electromagnetic energy is to be used for deep tissue targets away from natural orifices, absorption lengths restrict the wavelengths to those of microwaves or radiofrequency waves, depending on the depth of the target tissue. However, ultrasound is to be preferred to long wavelength electromagnetic radiation for deep tissue targets away from natural orifices.

The ultrasound or electromagnetic radiation is pulsed so as to create a thermal time-course in the tissue that stimulates HSP production or activation and facilitates protein repair without causing damage to the cells and tissue being treated. The area and/or volume of the treated tissue is also controlled and minimized so that the temperature spikes are on the order of several degrees, e.g. approximately 10° C., while maintaining the long-term rise in temperature to be less than the FDA mandated limit, such as 1° C. It has been found that if too large of an area or volume of tissue is treated, the increased temperature of the tissue cannot be diffused sufficiently quickly enough to meet the FDA requirements. However, limiting the area and/or volume of the treated tissue as well as creating a pulsed source of energy accomplishes the goals of the present invention of stimulating HSP activation or production by heating or otherwise stressing the cells and tissue, while allowing the treated cells and tissues to dissipate any excess heat generated to within acceptable limits.

Figure 24:
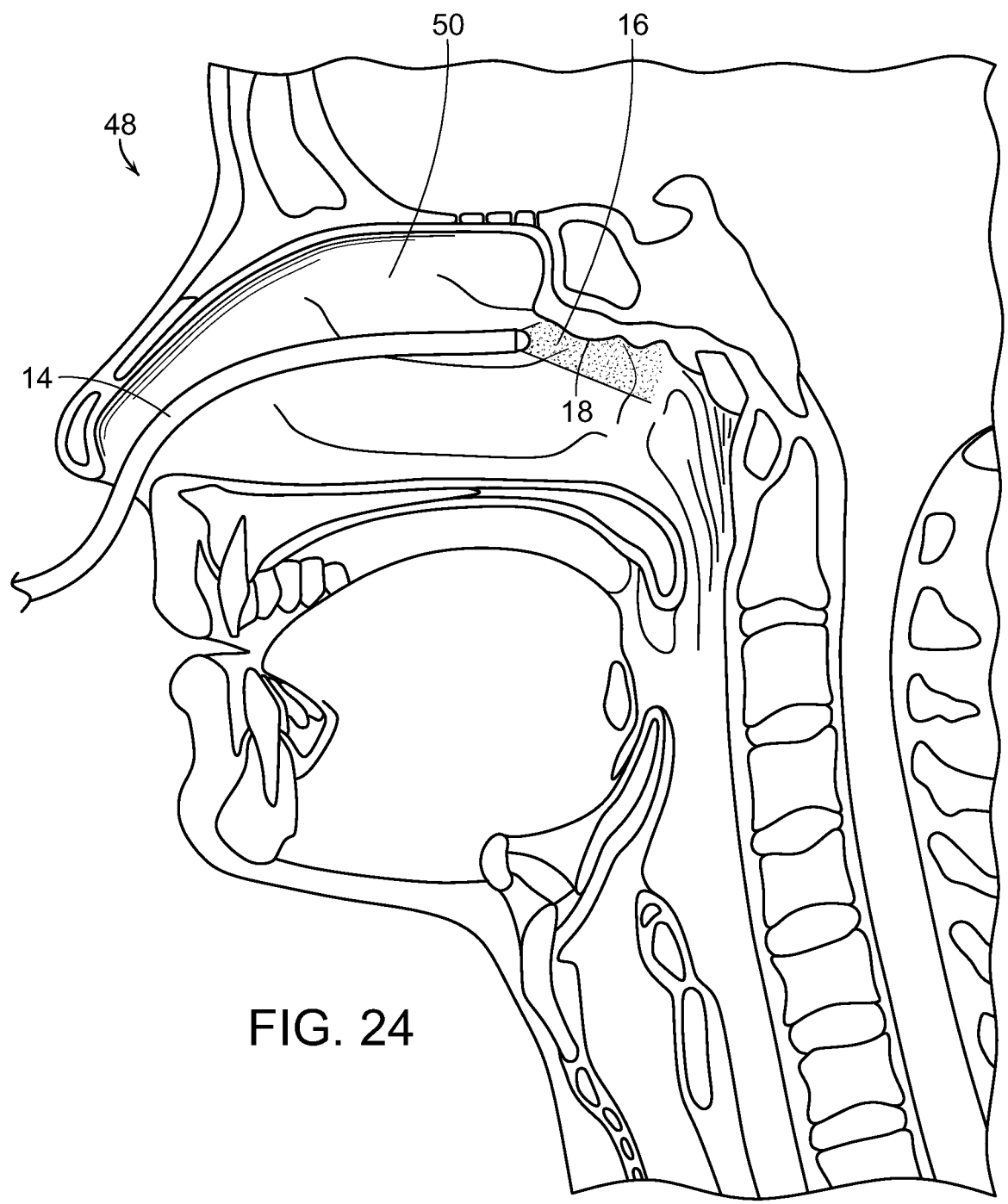
FIG. 24 is a cross-sectional and diagrammatic view of an end of an endoscope inserted into the nasal cavity and treating tissue therein, in accordance with the present invention.

It is believed that stimulating HSP production in accordance with the present invention can be effectively utilized in treating a wide array of tissue abnormalities, ailments, and even infections. For example, the viruses that cause colds primarily affect a small port of the respiratory epithelium in the nasal passages and nasopharynx. Similar to the retina, the respiratory epithelium is a thin and clear tissue. With reference to FIG. 24, a cross-sectional view of a human head 48 is shown with an endoscope 14 inserted into the nasal cavity 50 and energy 16, such as laser light or the like, being directed to tissue 18 to be treated within the nasal cavity 50. The tissue 18 to be treated could be within the nasal cavity 50, including the nasal passages, and nasopharynx.

To assure absorption of the laser energy, or other energy source, the wavelength can be adjusted to an infrared (IR) absorption peak of water, or an adjuvant dye can be used to serve as a photosensitizer. In such a case, treatment would then consist of drinking, or topically applying, the adjuvant, waiting a few minutes for the adjuvant to permeate the surface tissue, and then administering the laser light or other energy source 16 to the target tissue 18 for a few seconds, such as via optical fibers in an endoscope 14, as illustrated in FIG. 24. To provide comfort of the patient, the endoscope 14 could be inserted after application of a topical anesthetic. If necessary, the procedure could be repeated periodically, such as in a day or so.

The treatment would stimulate the activation or production of heat shock proteins and facilitate protein repair without damaging the cells and tissues being treated. As discussed above, certain heat shock proteins have been found to play an important role in the immune response as well as the well-being of the targeted cells and tissue. The source of energy could be monochromatic laser light, such as 810 nm wavelength laser light, administered in a manner similar to that described in the above-referenced patent applications, but administered through an endoscope or the like, as illustrated in FIG. 24. The adjuvant dye would be selected so as to increase the laser light absorption. While this comprises a particularly preferred method and embodiment of performing the invention, it will be appreciated that other types of energy and delivery means could be used to achieve the same objectives in accordance with the present invention.

Figure 25:
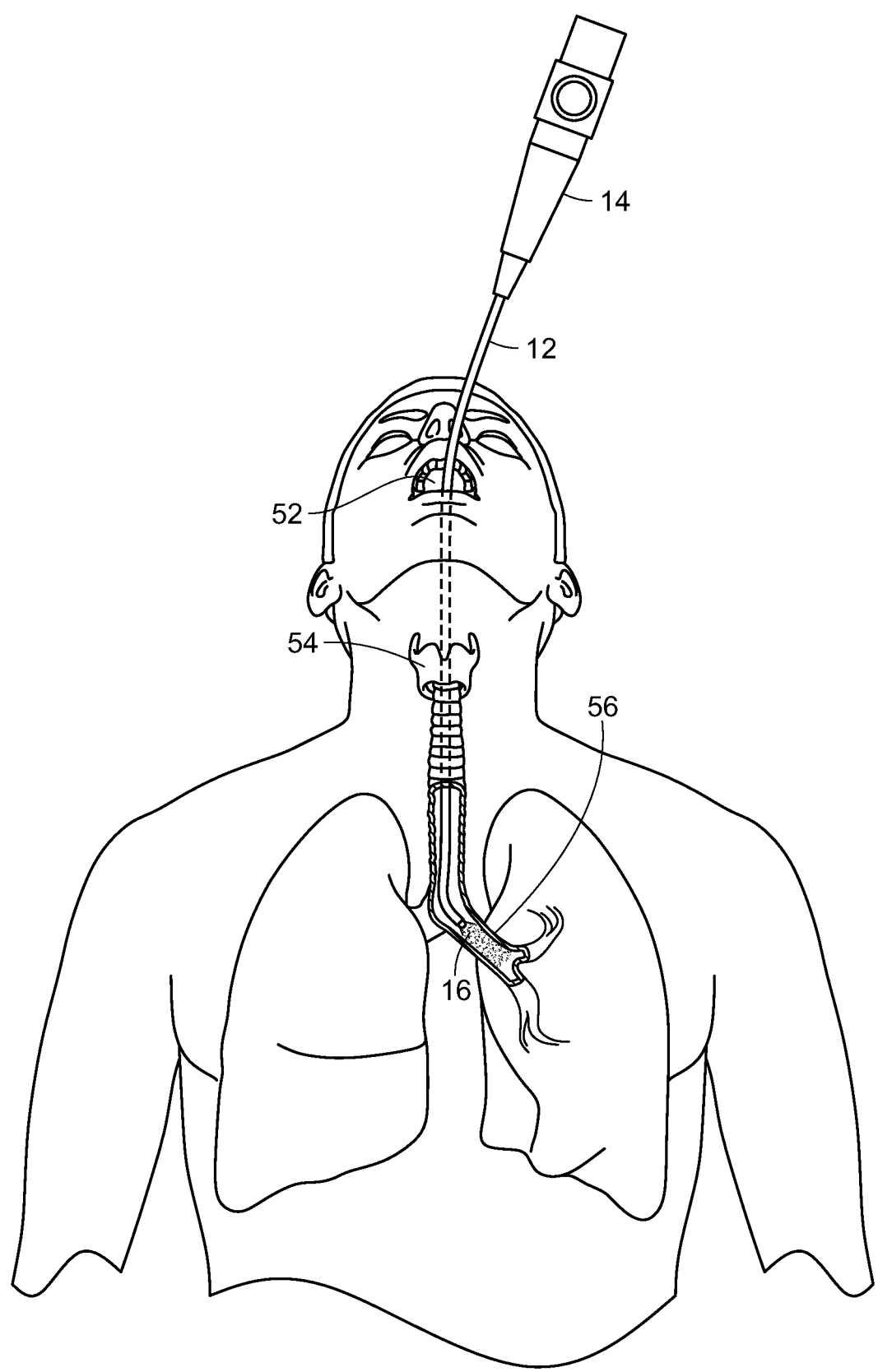
FIG. 25 is a diagrammatic and partially cross-sectioned view of a bronchoscope extending through the trachea and into the bronchus of a lung and providing treatment thereto, in accordance with the present invention.

With reference now to FIG. 25, a similar situation exists for the flu virus, where the primary target is the epithelium of the upper respiratory tree, in segments that have diameters greater than about 3.3 mm, namely, the upper six generations of the upper respiratory tree. A thin layer of mucous separates the targeted epithelial cells from the airway lumen, and it is in this layer that the antigen-antibody interactions occur that result in inactivation of the virus.

With continuing reference to FIG. 25, the flexible light tube 12 of a bronchoscope 14 is inserted through the individual's mouth 52 through the throat and trachea 54 and into a bronchus 56 of the respiratory tree. There the laser light or other energy source 16 is administered and delivered to the tissue in this area of the uppermost segments to treat the tissue and area in the same manner described above with respect to FIG. 24. It is contemplated that a wavelength of laser or other energy would be selected so as to match an IR absorption peak of the water resident in the mucous to heat the tissue and stimulate HSP activation or production and facilitate protein repair, with its attendant benefits.

Figure 26:
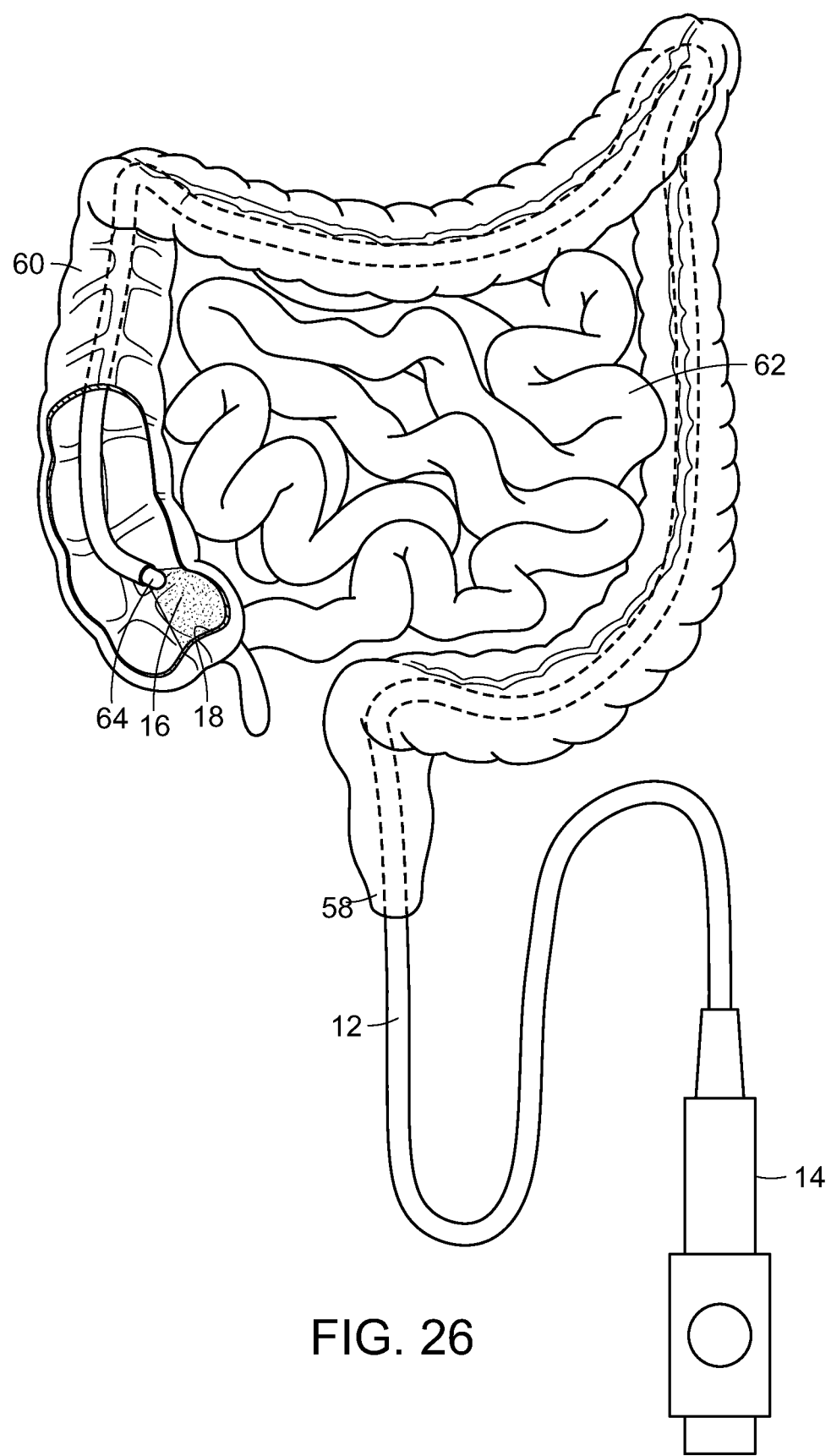
FIG. 26 is a diagrammatic view of a colonoscope providing photostimulation to an intestinal or colon area of the body, in accordance with the present invention.

With reference now to FIG. 26, a colonoscope 14 could have flexible optical tube 12 thereof inserted into the anus and rectum 58 and into either the large intestine 60 or small intestine 62 so as to deliver the selected laser light or other energy source 16 to the area and tissue to be treated, as illustrated. This could be used to assist in treating colon cancer as well as other gastrointestinal issues.

Typically, the procedure could be performed similar to a colonoscopy in that the bowel would be cleared of all stool, and the patient would lie on his/her side and the physician would insert the long, thin light tube portion 12 of the colonoscope 14 into the rectum and move it into the area of the colon, large intestine 60 or small intestine 64 to the area to be treated. The physician could view through a monitor the pathway of the inserted flexible member 12 and even view the tissue at the tip of the colonoscope 14 within the intestine, so as to view the area to be treated. Using one of the other fiber optic or light tubes, the tip 64 of the scope would be directed to the tissue to be treated and the source of laser light or other radiation 16 would be delivered through one of the light tubes of the colonoscope 14 to treat the area of tissue to be treated, as described above, in order to stimulate HSP activation or production in that tissue 18.

Figure 27:
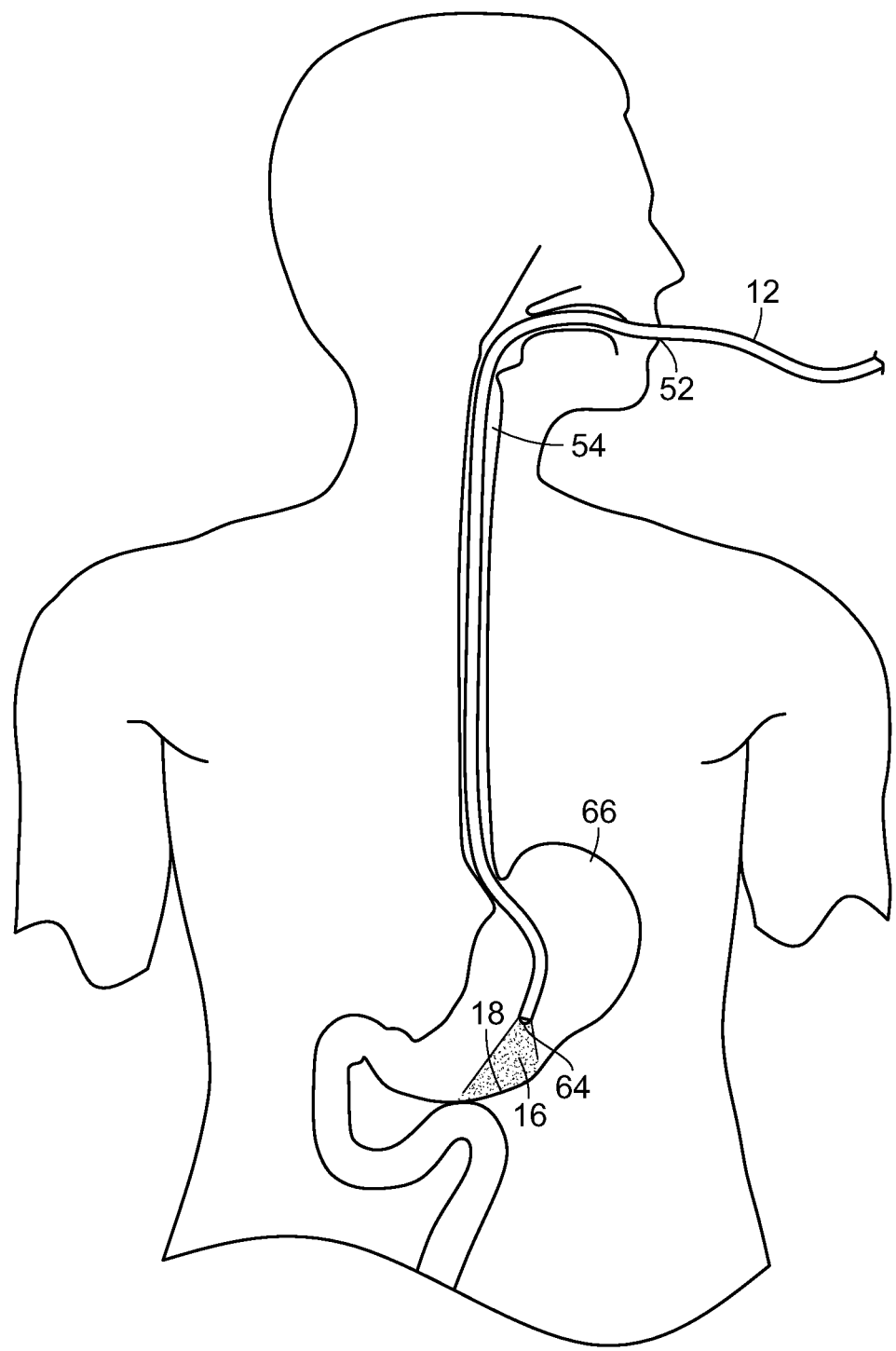
FIG. 27 is a diagrammatic view of an endoscope inserted into a stomach and providing treatment thereto, in accordance with the present invention.

With reference now to FIG. 27, another example in which the present invention can be advantageously used is what is frequently referred to as "leaky gut" syndrome, a condition of the gastrointestinal (GI) tract marked by inflammation and other metabolic dysfunction. Since the GI tract is susceptible to metabolic dysfunction similar to the retina, it is anticipated that it will respond well to the treatment of the present invention. This could be done by means of subthreshold, diode micropulse laser (SDM) treatment, as discussed above, or by other energy sources and means as discussed herein and known in the art.

With continuing reference to FIG. 27, the flexible light tube 12 of an endoscope or the like is inserted through the patient's mouth 52 through the throat and trachea area 54 and into the stomach 66, where the tip or end 64 thereof is directed towards the tissue 18 to be treated, and the laser light or other energy source 16 is directed to the tissue 18. It will be appreciated by those skilled in the art that a colonoscope could also be used and inserted through the rectum 58 and into the stomach 66 or any tissue between the stomach and the rectum.

If necessary, a chromophore pigment could be delivered to the GI tissue orally to enable absorption of the radiation. If, for instance, unfocused 810 nm radiation from a laser diode or LED were to be used, the pigment would have an absorption peak at or near 810 nm. Alternatively, the wavelength of the energy source could be adjusted to a slightly longer wavelength at an absorption peak of water, so that no externally applied chromophore would be required.

Figure 28:
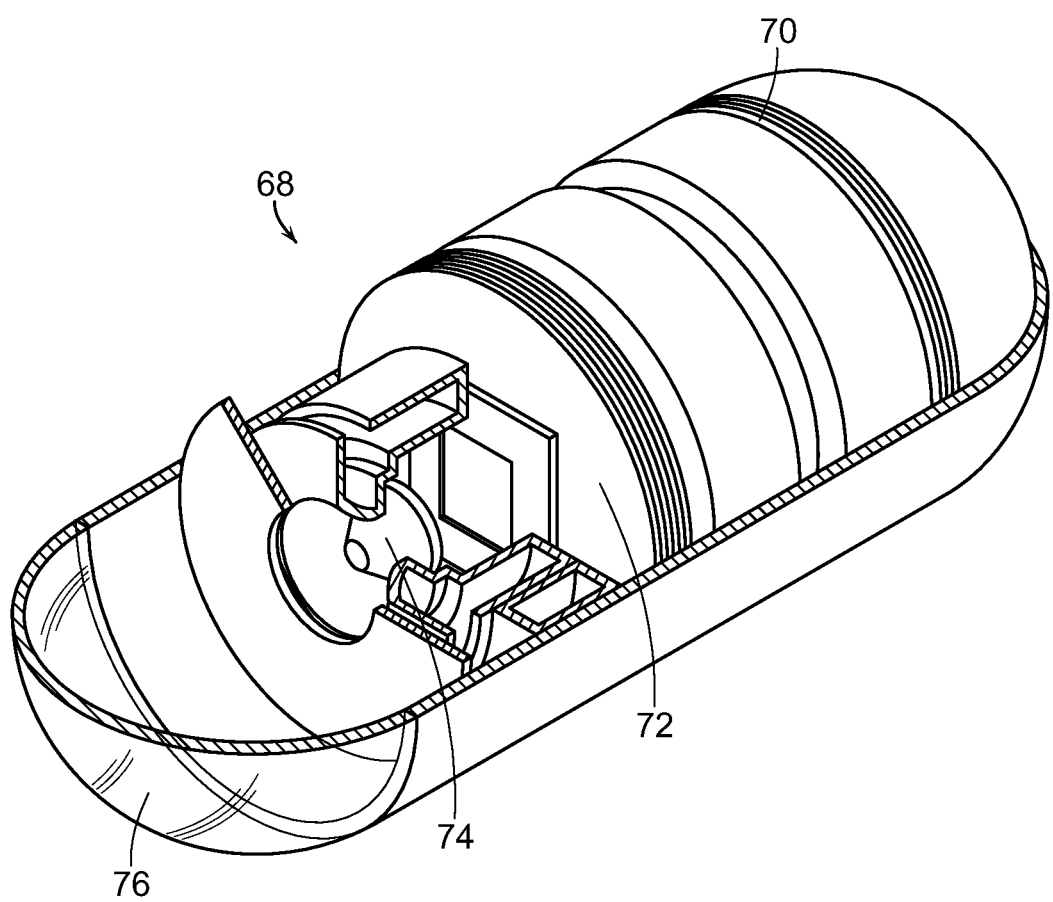
FIG. 28 is a partially sectioned perspective view of a capsule endoscope, used in accordance with the present invention.

It is also contemplated by the present invention that a capsule endoscope 68, such as that illustrated in FIG. 28, could be used to administer the radiation and energy source in accordance with the present invention. Such capsules are relatively small in size, such as approximately one inch in length, so as to be swallowed by the patient. As the capsule or pill 68 is swallowed and enters into the stomach and passes through the GI tract, when at the appropriate location, the capsule or pill 68 could receive power and signals, such as via antenna 70, so as to activate the source of energy 72, such as a laser diode and related circuitry, with an appropriate lens 74 focusing the generated laser light or radiation through a radiation-transparent cover 76 and onto the tissue to be treated. It will be understood that the location of the capsule endoscope 68 could be determined by a variety of means such as external imaging, signal tracking, or even by means of a miniature camera with lights through which the doctor would view images of the GI tract through which the pill or capsule 68 was passing through at the time. The capsule or pill 68 could be supplied with its own power source, such as by virtue of a battery, or could be powered externally via an antenna, such that the laser diode 72 or other energy generating source create the desired wavelength and pulsed energy source to treat the tissue and area to be treated.

As in the treatment of the retina in previous applications, the radiation would be pulsed to take advantage of the micropulse temperature spikes and associated safety, and the power could be adjusted so that the treatment would be completely harmless to the tissue. This could involve adjusting the peak power, pulse times, and repetition rate to give spike temperature rises on the order of 10° C., while maintaining the long term rise in temperature to be less than the FDA mandated limit of 1° C. If the pill form 68 of delivery is used, the device could be powered by a small rechargeable battery or over wireless inductive excitation or the like. The heated/stressed tissue would stimulate activation or production of HSP and facilitate protein repair, and the attendant benefits thereof.

From the foregoing examples, the technique of the present invention is limited to the treatment of conditions at near body surfaces or at internal surfaces easily accessible by means of fiber optics or other optical delivery means. The reason that the application of SDM to activate HSP activity is limited to near surface or optically accessibly regions of the body is that the absorption length of IR or visible radiation in the body is very short. However, there are conditions deeper within tissue or the body which could benefit from the present invention. Thus, the present invention contemplates the use of ultrasound and/or radio frequency (RF) and even shorter wavelength electromagnetic (EM) radiation such as microwave which have relatively long absorption lengths in body tissue. The use of pulsed ultrasound is preferable to RF electromagnetic radiation to activate remedial HSP activity in abnormal tissue that is inaccessible to surface SDM or the like. Pulsed ultrasound sources can also be used for abnormalities at or near surfaces as well.

Figure 29:
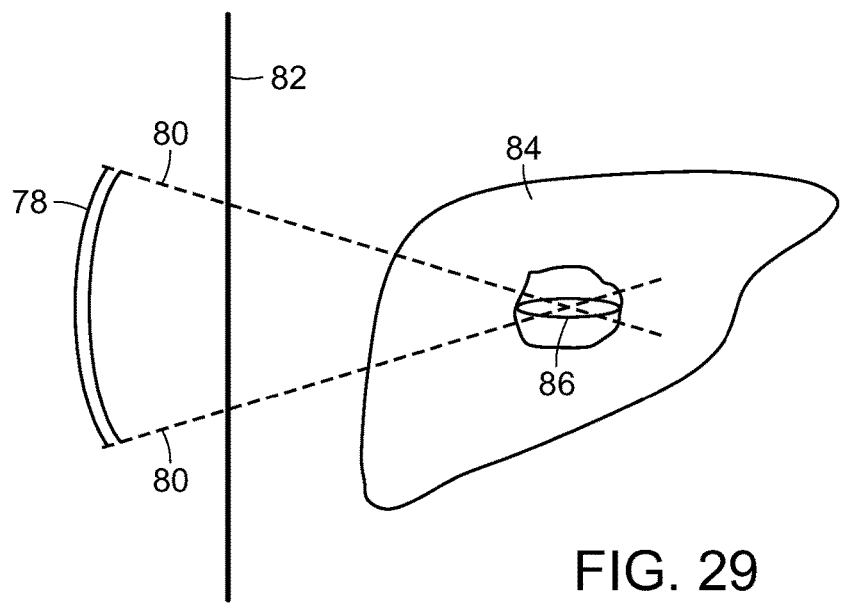
FIG. 29 is a diagrammatic view of a pulsed high intensity focused ultrasound for treating tissue internal the body, in accordance with the present invention.

With reference now to FIG. 29, with ultrasound, a specific region deep in the body can be specifically targeted by using one or more beams that are each focused on the target site. The pulsating heating will then be largely only in the targeted region where the beams are focused and overlap.

As illustrated in FIG. 29, an ultrasound transducer 78 or the like generates a plurality of ultrasound beams 80 which are coupled to the skin via an acoustic-impedance-matching gel, and penetrate through the skin 82 and through undamaged tissue in front of the focus of the beams 80 to a target organ 84, such as the illustrated liver, and specifically to a target tissue 86 to be treated where the ultrasound beams 80 are focused. As mentioned above, the pulsating heating will then only be at the targeted, focused region 86 where the focused beams 80 overlap. The tissue in front of and behind the focused region 86 will not be heated or affected appreciably.

The present invention contemplates not only the treatment of surface or near surface tissue, such as using the laser light or the like, deep tissue using, for example, focused ultrasound beams or the like, but also treatment of blood diseases, such as sepsis. As indicated above, focused ultrasound treatment could be used both at surface as well as deep body tissue, and could also be applied in this case in treating blood. However, it is also contemplated that the SDM and similar treatment options which are typically limited to surface or near surface treatment of epithelial cells and the like be used in treating blood diseases at areas where the blood is accessible through a relatively thin layer of tissue, such as the earlobe.

Figure 30:
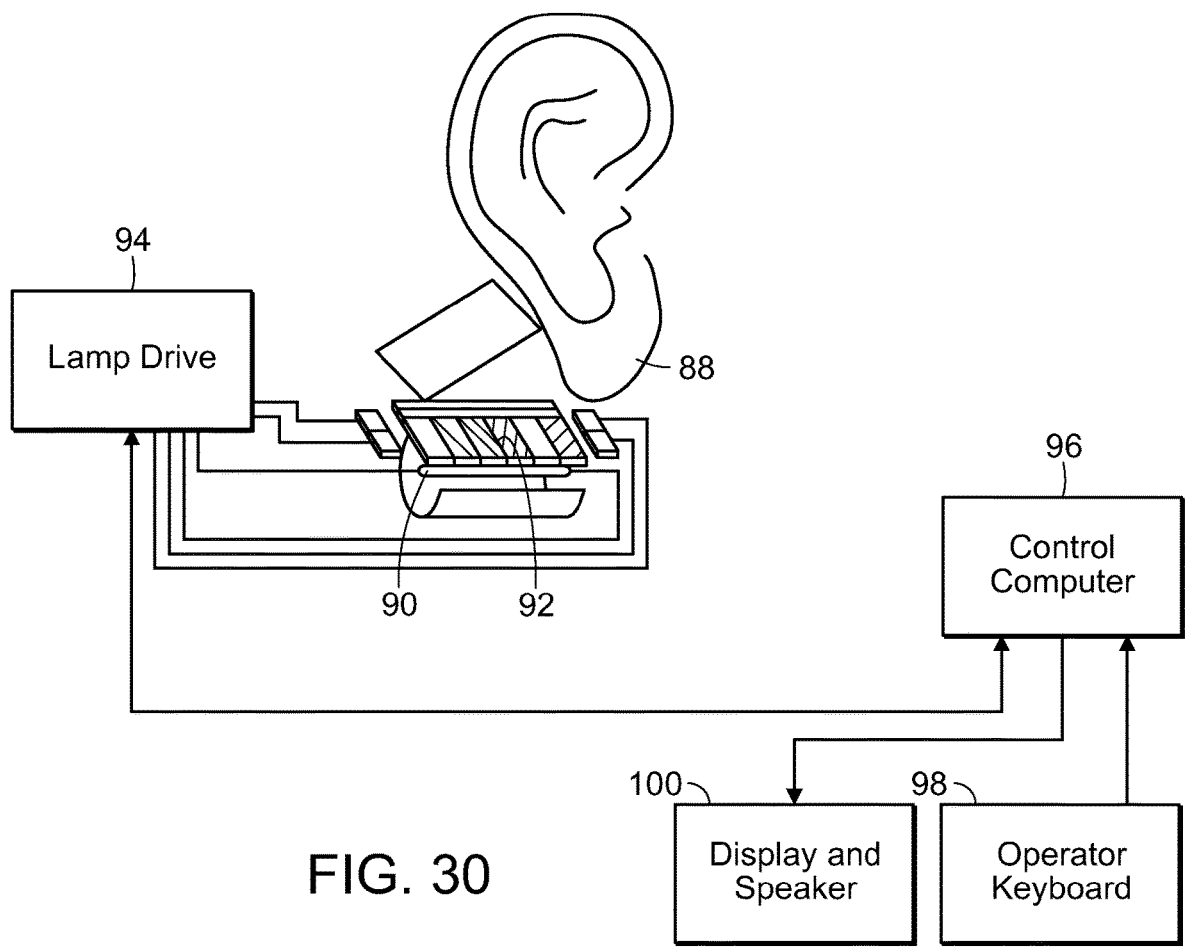
FIG. 30 is a diagrammatic view for delivering therapy to the bloodstream of a patient, through an earlobe, in accordance with the present invention.
Figure 31:
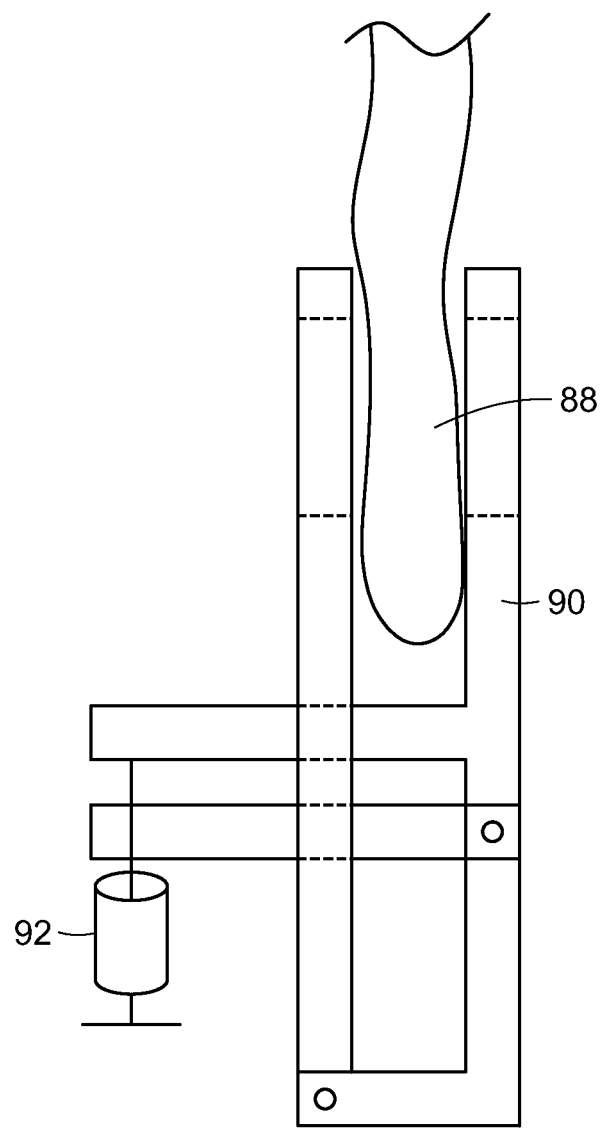
FIG. 31 is a cross-sectional view of a stimulating therapy device of the present invention used in delivering photostimulation to the blood, via an earlobe, in accordance with the present invention.

With reference now to FIGS. 30 and 31, treatment of blood disorders simply requires the transmission of SDM or other electromagnetic radiation or ultrasound pulses to the earlobe 88, where the SDM or other radiation source of energy could pass through the earlobe tissue and into the blood which passes through the earlobe. It would be appreciated that this approach could also take place at other areas of the body where the blood flow is relatively high and/or near the tissue surface, such as fingertips, inside of the mouth or throat, etc.

With reference again to FIGS. 30 and 31, an earlobe 88 is shown adjacent to a clamp device 90 configured to transmit SDM radiation or the like. This could be, for example, by means of one or more laser diodes 92 which would transmit the desired frequency at the desired pulse and pulse train to the earlobe 88. Power could be provided, for example, by means of a lamp drive 94. Alternatively, the lamp drive 94 could be the actual source of laser light, which would be transmitted through the appropriate optics and electronics to the earlobe 88. The clamp device 90 would merely be used to clamp onto the patient's earlobe and cause that the radiation be constrained to the patient's earlobe 88. This may be by means of mirrors, reflectors, diffusers, etc. This could be controlled by a control computer 96, which would be operated by a keyboard 98 or the like. The system may also include a display and speakers 100, if needed, for example if the procedure were to be performed by an operator at a distance from the patient.

The proposed treatment with a train of electromagnetic or ultrasound pulses has two major advantages over earlier treatments that incorporate a single short or sustained (long) pulse. First, the short (preferably subsecond) individual pulses in the train activate cellular reset mechanisms like HSP activation with larger reaction rate constants than those operating at longer (minute or hour) time scales. Secondly, the repeated pulses in the treatment provide large thermal spikes (on the order of 10,000) that allow the cell's repair system to more rapidly surmount the activation energy barrier that separates a dysfunctional cellular state from the desired functional state. The net result is a "lowered therapeutic threshold" in the sense that a lower applied average power and total applied energy can be used to achieve the desired treatment goal.

Although several embodiments have been described in detail for purposes of illustration, various modifications may be made without departing from the scope and spirit of the invention. Accordingly, the invention is not to be limited, except as by the appended claims.

What is claimed is:

1. A method for heat treating biological tissues, comprising the steps of:
   providing a pulsed energy source having preselected energy parameters including wavelength or frequency, duty cycle, power and pulse train duration; and
   applying the pulsed energy source to or through skin, or a respiratory or a digestive tract membrane and to a target tissue, to heat the target tissue for less than 1 second and raise the target tissue temperature between six and eleven degrees Celsius at least during application of the pulsed energy source to the target tissue to achieve a therapeutic effect while maintaining a target tissue total temperature increase over six minutes or less at or below one degree Celsius so as not to damage the target tissue;
   wherein the pulsed energy source is directed to a blood supply close to the surface of the skin or the respiratory membrane or the digestive tract membrane so as to treat a disease or disorder of the blood.

2. The method of claim 1, wherein the applying step comprises the step of stimulating heat shock protein activation in the target tissue.

3. The method of claim 1, wherein the pulsed energy source energy parameters are selected so that 20 to 40 joules of energy is absorbed by each cubic centimeter of the target tissue.

4. The method of claim 1, wherein the applying the pulsed energy source step comprises inserting a device into a cavity of a body to apply the pulsed energy source to the target tissue.

5. The method of claim 1, wherein the pulsed energy source comprises laser light.

6. The method of claim 1, wherein the pulsed energy source comprises a radio frequency between three to six megahertz, a duty cycle of between 2.5% to 5%, and a pulse train duration of between 0.2 to 0.4 seconds.

7. The method of claim 6, wherein the radio frequency is generated with a device having a coil radii of between 2 and 6 mm and between 13 and 57 amp turns.

8. The method of claim 1, wherein the pulsed energy source comprises a microwave frequency of between 10 to 20 GHz, a pulse train duration of between 0.2 and 0.6 seconds, and a duty cycle of between 2% to 5%.

9. The method of claim 8, wherein the microwave has an average power of between approximately 8 and 52 watts.

10. The method of claim 1, wherein the pulsed energy source comprises a pulsed light beam having a wavelength of between 530 nm to 1300 nm, a duty cycle of less than 10%, and a pulse train duration between 0.1 and 0.6 seconds.

11. The method of claim 10, wherein the pulsed light beam has a wavelength of between 800 nm and 1000 nm and a power of between 0.5 and 74 watts.

12. The method of claim 1, wherein the pulsed energy source comprises pulsed ultrasound having a frequency of between 1 MHz and 5 MHz, a train duration of between 0.1 and 0.5 seconds and a duty cycle of between 2% to 10%.

13. The method of claim 12, wherein the ultrasound has a power of between 0.46 and 28.6 watts.

14. The method of claim 4, wherein the device is inserted into a nasal cavity, mouth, throat, lung, gastrointestinal tract, stomach, intestine, colon or rectum.

* * * * *